(12) United States Patent
O'Malley et al.

(10) Patent No.: US 8,663,275 B2
(45) Date of Patent: *Mar. 4, 2014

(54) CLINICAL AND SURGICAL SYSTEM AND METHOD FOR MOVING AND STRETCHING PLASTIC TISSUE

(75) Inventors: Michael T. O'Malley, Appleton (CA); Michael S. G. Bell, Ottawa (CA); Timothy Maxwell, Carp (CA); James Henderson, Carp (CA)

(73) Assignee: Canica Design Inc., Almonte, Ontario (CA)

( * ) Notice: Subject to any disclaimer, the term of this patent is extended or adjusted under 35 U.S.C. 154(b) by 1151 days.

This patent is subject to a terminal disclaimer.

(21) Appl. No.: 12/040,560

(22) Filed: Feb. 29, 2008

(65) Prior Publication Data

US 2008/0147115 A1  Jun. 19, 2008

Related U.S. Application Data

(60) Division of application No. 10/192,326, filed on Jul. 9, 2002, now Pat. No. 7,361,185, which is a continuation-in-part of application No. PCT/IB01/00796, filed on May 9, 2001.

(60) Provisional application No. 60/249,766, filed on Nov. 17, 2000, provisional application No. 60/202,739, filed on May 10, 2000.

(51) Int. Cl.
    *A61B 17/08* (2006.01)
(52) U.S. Cl.
    USPC .......................................................... 606/216

(58) Field of Classification Search
    USPC ................................................ 606/213–216
    See application file for complete search history.

(56) References Cited

U.S. PATENT DOCUMENTS

| 261,531 A | 7/1882 | Cook |
| 355,092 A | 12/1886 | Knapp |
| 363,538 A | 5/1887 | Penny |
| 563,833 A | 7/1896 | Zahl |
| 667,939 A | 2/1901 | Frye |
| 701,313 A | 6/1902 | Duffy |

(Continued)

FOREIGN PATENT DOCUMENTS

| CN | 2676918 Y | 2/2005 |
| DE | 10138793 | 2/2003 |

(Continued)

OTHER PUBLICATIONS

European Patent Application No. 06759744.3, Office Action dated Jan. 21, 2010.

(Continued)

*Primary Examiner* — Corrine M McDermott
*Assistant Examiner* — Son Dang
(74) *Attorney, Agent, or Firm* — Kilpatrick Townsend & Stockton LLP; John S. Pratt; Camilla C. Williams

(57) ABSTRACT

A system and method of moving and stretching plastic tissue using dynamic force. A preferably non-reactive force applying component is adjustably attachable to one or more tissue attachment structures for securing the force applying component to the plastic tissue, providing a self adjusting system that is capable of exerting relatively constant tension over a certain distance.

18 Claims, 14 Drawing Sheets

(56) References Cited

U.S. PATENT DOCUMENTS

| | | | |
|---|---|---|---|
| 1,074,413 A | 9/1913 | De Baun | |
| 1,434,723 A | 11/1922 | Triay | |
| 1,969,188 A * | 8/1934 | Spicer | 606/216 |
| 2,018,517 A | 10/1935 | Fetter | |
| 2,196,296 A | 4/1940 | Flynn | |
| 2,226,546 A | 12/1940 | Bower | |
| 2,387,131 A | 10/1945 | Fernandez | |
| 2,586,488 A | 2/1952 | Smith | |
| 2,751,909 A | 6/1956 | Weitzner | |
| 2,845,925 A | 8/1958 | Gaetan | |
| 2,887,005 A | 5/1959 | Fromm | |
| 3,402,716 A | 9/1968 | Baxter | |
| 3,454,011 A * | 7/1969 | Wagner | 606/224 |
| 3,520,306 A | 7/1970 | Gardner et al. | |
| 3,698,395 A | 10/1972 | Hasson | |
| 3,762,401 A | 10/1973 | Tupper | |
| 3,762,418 A * | 10/1973 | Wasson | 606/226 |
| 3,783,873 A | 1/1974 | Jacobs | |
| 3,823,709 A | 7/1974 | McGuire | |
| 3,926,193 A * | 12/1975 | Hasson | 606/218 |
| 3,976,079 A | 8/1976 | Samuels et al. | |
| 3,998,217 A | 12/1976 | Trumbull et al. | |
| 4,430,991 A | 2/1984 | Darnell | |
| 4,531,521 A | 7/1985 | Haverstock | |
| 4,535,772 A * | 8/1985 | Sheehan | 606/218 |
| 4,539,990 A | 9/1985 | Stivala | |
| 4,605,005 A | 8/1986 | Sheehan | |
| 4,693,236 A | 9/1987 | Leprevost | |
| 4,742,826 A | 5/1988 | McLorg | |
| 4,780,168 A | 10/1988 | Beisang et al. | |
| 4,825,866 A | 5/1989 | Pierce | |
| 4,917,112 A | 4/1990 | Kalt | |
| 5,009,663 A | 4/1991 | Broome et al. | |
| 5,013,243 A | 5/1991 | Tanaka et al. | |
| 5,029,371 A | 7/1991 | Rosenblood et al. | |
| 5,036,866 A | 8/1991 | Eldrige et al. | |
| 5,041,129 A | 8/1991 | Hayhurst et al. | |
| 5,111,558 A | 5/1992 | Ridley et al. | |
| 5,123,843 A | 6/1992 | Van der Zet et al. | |
| 5,127,412 A * | 7/1992 | Cosmetto et al. | 128/898 |
| 5,195,538 A | 3/1993 | Eldridge, Jr. et al. | |
| 5,234,462 A * | 8/1993 | Pavletic | 606/215 |
| 5,259,835 A | 11/1993 | Clark et al. | |
| 5,263,971 A | 11/1993 | Hirshowitz et al. | |
| 5,269,809 A | 12/1993 | Hayhurst et al. | |
| 5,336,219 A | 8/1994 | Krantz | |
| 5,384,103 A | 1/1995 | Miller | |
| 5,406,838 A | 4/1995 | Miller | |
| 5,487,889 A | 1/1996 | Eckert et al. | |
| 5,507,775 A | 4/1996 | Ger et al. | |
| 5,534,010 A | 7/1996 | Peterson | |
| 5,538,500 A | 7/1996 | Peterson | |
| 5,546,961 A | 8/1996 | Harrison | |
| 5,580,344 A | 12/1996 | Hasson | |
| 5,593,379 A | 1/1997 | Rayman | |
| 5,628,724 A | 5/1997 | Debusk et al. | |
| 5,639,244 A | 6/1997 | Stricklin | |
| 5,649,960 A | 7/1997 | Pavletic | |
| 5,662,326 A | 9/1997 | Gebran | |
| 5,665,108 A * | 9/1997 | Galindo | 606/215 |
| 5,681,579 A | 10/1997 | Freeman | |
| 5,778,824 A | 7/1998 | Musgrave et al. | |
| 5,820,578 A | 10/1998 | Johansen | |
| 5,821,000 A | 10/1998 | Inui et al. | |
| 5,843,123 A * | 12/1998 | Brazeau | 606/213 |
| 5,871,357 A | 2/1999 | Tseng | |
| 5,876,333 A | 3/1999 | Bigliani et al. | |
| 5,927,022 A | 7/1999 | Hirakawa et al. | |
| 5,968,097 A * | 10/1999 | Frechet et al. | 623/15.12 |
| 5,972,022 A | 10/1999 | Huxel | |
| 6,066,160 A * | 5/2000 | Colvin et al. | 606/232 |
| 6,102,854 A | 8/2000 | Cartier et al. | |
| 6,106,544 A | 8/2000 | Brazeau | |
| 6,119,318 A | 9/2000 | Maurer | |
| 6,149,669 A | 11/2000 | Li | |
| 6,174,323 B1 | 1/2001 | Biggs et al. | |
| 6,190,312 B1 | 2/2001 | Fowler, Jr. | |
| 6,219,891 B1 | 4/2001 | Maurer et al. | |
| 6,267,744 B1 | 7/2001 | Roberts et al. | |
| 6,329,564 B1 | 12/2001 | Lebner | |
| 6,432,074 B1 | 8/2002 | Ager et al. | |
| 6,478,656 B1 | 11/2002 | Khouri | |
| 6,517,563 B1 | 2/2003 | Paolitto et al. | |
| 7,361,185 B2 | 4/2008 | O'Malley et al. | |
| 7,429,265 B2 | 9/2008 | O'Malley et al. | |
| 2005/0020957 A1 | 1/2005 | Lebner | |
| 2005/0085757 A1 | 4/2005 | Santanello | |
| 2005/0182443 A1 | 8/2005 | Jonn et al. | |

FOREIGN PATENT DOCUMENTS

| | | |
|---|---|---|
| EP | 0296669 | 6/1987 |
| EP | 0279534 | 8/1988 |
| EP | 0792622 | 2/1997 |
| FR | 2661821 | 11/1991 |
| GB | 328741 | 5/1930 |
| GB | 2188850 | 10/1987 |
| GB | 2215771 | 9/1989 |
| WO | WO-92/15251 | 9/1992 |
| WO | WO-9317633 | 9/1993 |
| WO | WO-96/10954 | 4/1996 |
| WO | WO-96/24316 | 8/1996 |
| WO | WO-97/13450 | 4/1997 |
| WO | WO-99/05973 | 2/1999 |
| WO | WO-99/35974 | 7/1999 |
| WO | WO-00/10466 | 3/2000 |
| WO | WO-00/32111 | 6/2000 |
| WO | WO-01/39693 | 6/2001 |
| WO | WO-01/85035 | 11/2001 |
| WO | WO-2005/079674 | 9/2005 |
| WO | WO-2005/112852 | 12/2005 |

OTHER PUBLICATIONS

U.S. Appl. No. 11/223,324, Office Action dated Feb. 2, 2010.

Goodrich, Jr. M.D., E. O. "An Anchor Technique for Stay Sutures", *Surgery* Aug. 1968, vol. 64, No. 2, pp. 416-417.

Pavletic, M.M. "Use of an External Skin-Stretching Device for Wound Closure in Dogs and Cats", *J. Am. Vet. Med. Association*: 217(3): Aug. 1, 2000, pp. 350-354.

Ritzman, T.K. "Use of an External Skin Stretching Device in a Guinea Pig", *Exotic DVM*: 3(1): Jan. 2001, pp. 31-35.

International Search Report and Written Opinion for PCT/US2006/018544, mailed on Dec. 11, 2006.

European Search Report, European Patent Application No. 12150140, mailed Mar. 26, 2012.

* cited by examiner

CLINICAL AND SURGICAL SYSTEM AND METHOD FOR MOVING AND STRETCHING PLASTIC TISSUE

RELATED APPLICATION DATA

This application is a divisional of U.S. patent application Ser. No. 10/192,326, filed Jul. 9, 2002, which issued as U.S. Pat. No. 7,361,185. This application is also a continuation-in-part of International Application No. PCT/IB01/00796, filed Nov. 15, 2001, published in English under publication no. WO 01/85035.

FIELD OF THE INVENTION

This invention relates generally to systems and methods for moving and stretching plastic tissue and more particularly to systems and methods for moving and stretching such tissue that exert a relatively constant tension over a given distance and that are easily adjustable.

BACKGROUND

In general, surgery and surgical treatment involve one or both of tissue separation and tissue joining. In surgery, medical treatment, and medical research, it is desirable to retract tissue, stabilize tissue, and present tissue in a variety of specific orientations to provide access to the area under investigation or repair, ideally in a method that creates minimal trauma beyond what is necessary for exposure and visualization of the operative area. In other words, it is desirable to exert a force on a tissue structure by reference either to some or all of the other tissue of which it is to become a part, as in the case of a transplant. Such an exertion of force for the purpose of tissue manipulation may be accomplished through very simple and short series of elements or through complex and lengthy series of elements that may or may not include gravity as a significant element. Examples of simple series in which gravity is not a significant element include sutures and staples (tissue joining) and a rib spreader (tissue separation).

Moving tissue presents unique challenges, as tissues often resist joining, or closure, depending on the nature of the tissue structure, the circumstances of the tissue separation, and general patient health. Complications related to wound closure and healing generally result from major forces, minor forces and/or compromised healing responses. Major forces are retractive forces created beyond the viscoelastic properties of the tissue, and may be created by: (1) increased internal volume, such as in the case of obesity, which elevates containment forces on the skin system; (2) changes in aspect ratio, such as increased abdominal circumference created in a prone, non-ambulatory patients due to muscular atrophy; (3) respiratory muscular activity; (4) muscular response; (5) loss of fascia structure; (6) muscular-skeletal deformation; (7) fleshy appendages; (8) tumors; and (9) severe burns.

Minor forces are internal forces created by the viscoelastic properties of the tissue, which can cause the skin to retract. Elastic tissues, such as skin, return to a minimum elastic, or relaxed, state when released from tension. In this relaxed state, tissue cells have a spherical shape, cell walls are thick and strong, and cell surface tensions are minimized and balanced. A cell in this minimum elastic state will remain relaxed, demonstrating behavior similar to a non-elastic material. The force required to elongate a cell in this state often approaches a force that will rupture or sheer intercellular bonds, causing localized failures or tears. Soft tissue in this minimum elastic state provides minimum surface coverage and has the highest reluctance to stretch. It is believed that a gentle but constant force below the sheer force threshold applied to tissue in combination with adequate hydration will, over time, restore certain tissues to original elastic state. Additionally, this force can be applied to stretch tissue past the point of equilibrium (normal elastic range) to the maximum elastic range and create the thinnest possible configuration, covering the maximum surface area. If intercellular pressures in the tissue do not exceed the point at which intercellular bonds are compromised, the tissue remains at the maximum elastic state as healthy tissue, and normal biological processes will build additional cells to restore normal skin thickness and tension, which is described below as biological creep.

Plastic tissues, such as skin and muscle, possess certain viscous and elastic rheological properties, and are therefore viscoelastic. Certain plastic tissues are able to increase surface area over time, which can be termed "creep." "Mechanical creep" is the elongation of skin with a constant load over time, while "biological creep" refers to the generation of new tissue due to a chronic stretching force. A constant and unrelenting force applied to a body tissue, such as skin or muscle, may result in both mechanical and biological creep. Mechanical creep restores the tension originally present but lost in the skin across the incision or wound by retensioning skin or soft tissue cells, thereby increasing skin coverage. Biological creep occurs more slowly and involves the creation of new tissue. Tissue expansion has long been part of the art of plastic surgery, traditionally accomplished with balloon-type tissue expanders embedded under the skin and externally inflated and increased over time to create expanded pockets of skin for procedures such as breast reconstruction after radical mastectomies, and stretching healthy tissue prior to plastic surgery for the creation of flaps for soft tissue closure.

Finally, compromised healing responses may complicate wound closure or healing. A surgical or other incision becomes a wound as soon as it falls behind normal healing protocol. Wound management, including treatment and care of large skin defects and severely retracted incisions, is an area of increasing importance to the health care community. An aging population and an increase in diseases related to obesity and inactivity have increased the occurrence of chronic wounds and place an increased burden on health care resources. Factors contributing to compromised wound healing include patient age, weight, nutritional status, dehydration, blood supply to the wound site, immune response, allergies to closure materials, chronic disease, debilitating injuries, localized or systemic infection, diabetes, and the use of immunosuppressive, corticosteroid or antineoplastic drugs, hormones, or radiation therapy. Chronic wounds include, but are not limited to: diabetic ulcers and other chronic ulcers; venous stastis ulcers; pressure sores or ulcers; burns; post traumatic lesions, such as post disarticulation, post debridement, cutaneous gangrene, post colectomy, crush wounds with ischemic necrosis; collagen disease, including rheumatoid arthritis; vasculitis (lesions and ulcers caused by arterial insufficiency); amputation; fasciotomy; post surgical dehiscence; post stemotomy; necrotising fasciitis; trauma; wounds having exposed plates or bones; scar revision; skin lesions; blunt abdominal trauma with perforations; pancreatitis; neuropathic ulcers; compartment syndrome; and other subacute or chronic wounds. Treatment and care of these defects is challenging due to difficulties in closure of open wounds.

Two common methods of closure of wounds and skin defects include split thickness skin grafting and gradual closure. A split thickness skin graft involves removing a partial layer of skin from a donor site, usually an upper leg or thigh, and leaving the dermis at the donor site to re-epithelialize. In this manner, a viable skin repair patch can be transferred or grafted to cover a wound area. The graft is often meshed, (which involves cutting the skin in a series of rows of offset longitudinal interdigitating cuts) allowing the graft to stretch to cover two or three times greater an area as well as provide wound drainage while healing. Normal biological function of the skin heals the holes after the graft has been accepted. A meshed graft of this type requires a smaller donor area than a conventional non-meshed or full thickness skin graft. However, these methods do not provide optimal cosmesis or quality of skin cover. Other disadvantages of this method include pain at the donor site, creation of an additional disfiguring wound, and complications associated with incomplete "take" of the graft. In addition, skin grafting often requires immobilization of the limb, which increases the likelihood of contractures. The additional operation and prolongation of hospital stay is an additional economic burden.

Gradual, or progressive, closure is a second method of closure. This technique may involve suturing vessel loops to the wound edge and drawing them together with large sutures in a fashion similar to lacing a shoe. In addition, the wound edges may be progressively approximated with suture or sterile paper tape. The advantages of this gradual, or progressive, technique are numerous: no donor site is required for harvest of a graft, limb mobility is maintained, and superior cosmetic result, more durable skin coverage, better protection from full skin thickness and the maintenance of normal skin sensation may all be achieved.

Existing devices for effecting a gradual closure have many disadvantages. Current methods and devices draw wound edges together using mechanical devices such as screw-actuated devices that require repeated periodic adjustment because a relatively small skin movement substantially eliminates much of the closure force. Widely used existing closure techniques involve use of relatively inelastic materials, such as sutures or surgical tape. Excessive tension may cut the skin or cause necrosis due to point loading of the tissue. Current solutions include suture bolsters, suture bridges, use of staples as anchors at the wound edge, and the use of ligature wire to distribute the load along the wound margins. These approaches all rely on static ribbon or suture material, which must repeatedly be readjusted in order to function effectively, and even with this constant readjustment, maintenance of near constant tension over time is difficult, if not impossible, to achieve. Widely used traditional gradual closure methods rely on static force through fixed distance reduction, and do not provide continuous or dynamic tension.

Many current methods of open wound reduction employ static or non-yielding devices such as sutures or hard approximators, which reduce the distance between the wound margins and rely on the skin's natural elasticity to compensate for movement. One problem with these devices has been that when they are at the point of being most effective, when the skin is at the point of maximum stretch, additional skin tension created through motion, such as breathing or walking, creates stress points where the mechanical fasteners meet the wound margins, causing tearing and wound edge necrosis. This has generally required patients to remain immobile during the course of treatment. Existing systems for treating animals need not consider cosmetic result to such a degree as the healthy patient typically masks the wound site with fur, but cosmesis is a critical criteria in the measurement of a successful result from the system in the human application.

One existing method for effecting closure of a wound utilizes a constant tension, low-grade force to draw wound edges together. One device for practicing this method includes a pair of hooks carried by a pair of sliders that move along a path pulled by a pair of springs. This spring device is enclosed in a plastic housing and is available having various curvatures. The sharp hooks used in this system may damage the skin. The constant force used is a dictated force that is not variable. Other closure devices use elastomeric material, including rubber bands and other types of compressive and non-compressive materials, to approximate wound margins. One kit requires bonding to the skin with an adhesive and also requires periodic adjustment to tighten the straps. Other known closure devices use hooks and elastic loops, which must be replaced with smaller elastic loops to maintain tension, or a motor power source to provide a tightening means. Finally, another current device consists of two surgical needles, two U-shaped lexan polycarbonate arms with hooks on the bottom surface, a threaded tension bar and a polycarbonate ruler. The needles are threaded along the wound margin and each arm is positioned above a needle, with the hooks piercing the skin and engaging the needles. The tension bar is then locked, and tension can be adjusted using the screw.

Existing methods of gradual wound closure fail to provide an effective gradual closure that restores original skin tensions lost across the wound. For example, one system has a single tension of 460 grams. In many instances, such as with the elderly or with compromised skin, this force is too great, resulting in localized failures, tears and necrosis. Many current devices are cumbersome, restrict patient mobility, must be completely removed for wound dressing and cleaning, and are usable in a relatively limited number of situations because of size constraints. Many also require a surgeon for reinstallation after removal for wound dressing. Finally, many current devices cannot readily be used for radial closure of wounds due to their limited ability to pull in a single direction along an overhead beam, thereby restricting their application to parallel pulls along the same axis.

SUMMARY OF THE INVENTION

This invention provides manipulation and control of tissue positions and tensions on a living person or animal, utilizing both tissue stretch and creep to restore and move any plastic tissues. This invention provides methods and devices for moving and stretching plastic tissue that are simple, easy to use, relatively inexpensive, extremely versatile, self-adjusting and capable of exerting relatively constant force or tension over a variety of distances and at various intersecting angles in wounds having simple or complex geometry.

Components of this invention exert a dynamic force on the tissue, providing and maintaining a maximum safe countertraction pressure or force across a wound margin or other area. The force remains below a level that would create localized failure at the wound edge. In this manner, controlled constant and unrelenting tension is created, which can be applied to counteract major or minor retraction forces or to achieve maximum mechanical and biological yields to move and stretch plastic tissue, including closure of large retracted skin defects. The tissue manipulation system of this invention utilizes force applying components (sometimes called "facs") coupled to force coupling components ("anchors") that couple to tissue the force exerted by the force applying component.

A force applying component normally serves two functions: (1) it stores energy in a manner that exerts force, and (2) it transmits the force. A force applying component can divide these functions in two, such as by (1) storing energy in a coiled expansion spring that is stretched to store energy and is attached to (2) a relatively inelastic cord, cable, wire, rod, filament, or thread positioned between the spring and an anchor to transmit force exerted by the spring to the anchor. In most embodiments of this invention the energy storage and force transmission functions are combined in a single elastic component such as a rod, filament, tube, or sheet of elastomeric material like silicone. Some embodiments, however, use relative inelastic materials to transmit force exerted by energy storage components like elastomeric materials or coiled or other metal or plastic springs.

An anchor for coupling force to tissue involves two components: (1) a tissue coupling component and (2) a component for coupling to a force applying component. Coupling of a fac can occur by passing a fac or a portion of a fac such as a suture through a hole penetrating tissue. However, such rudimentary coupling works poorly for several reasons, importantly including the extremely poor force distribution across the tissue and the absence of any practical means for adjusting the force exerted by the suture over a period of time.

The anchors of this invention generally separate the tissue coupling structure from the structure for attaching to a force applying component, thereby permitting optimization of each of the two anchor structures and adaptation of each anchor structure to a variety of different situations. The anchor structures of this invention for coupling to force applying components permit quick, easy attachment and reattachment of various facs, particularly including facs made of silicone, which is extremely difficult to secure. The tissue coupling structures and techniques of this invention include invasive structures such as flukes, staples and sutures, and tissue penetration by the force applying component. The tissue coupling structures also include non-invasive structures utilizing adhesive on plates and fabrics, among other alternatives.

Terms used herein are generally defined and, in some cases, abbreviated, as they are introduced. For convenience, selected terms are also defined here. A force applying component ("fac") generally stores energy in a manner that exerts force and transmits the force. An elastic force applying component ("efac") combines these two functions in a single elastic component. The term "elastomer" refers to relatively elastic material, such as silicone, or latex rubber. The term "non-reactive" is used to describe components that are either immunologically inert or hypoallergenic. Anchors are used to transmit force to the tissue to be moved or stretched and generally couple the fac to the tissue by providing structure for coupling to the fac and structure for coupling to the tissue.

This invention can be used to apply dynamic force for closure or remodeling of tissue to close dermal wounds, incisions, or defects that may be associated with a variety of conditions, as well as in the stretching of healthy skin in preparation for a skin graft, flap or other remodeling procedure. In the most simple use, such as closure of fasciotomies, the invention may be used to restore retracted skin to its original position. This invention may also be used to stretch skin to cover an area where some of the original skin has been lost, such as might be the case with a localized burn, ulcer, or contracture or to stretch skin prior to a skin graft, flap, or other plastic surgical procedure. Depending on age, general health, skin condition, degree of skin hydration, and other factors, most skin can be stretched about 20%. Under ideal conditions, skin can be stretched as much as 60% over a period of weeks. In rare circumstances, stretching as much as 100% is possible. The ability of the system to remodel the skin over time is useful in plastic surgery, as the preconceived parameters and limitations of the viscoelastic properties of the skin (previously expressed as langers lines) may be remodeled, creating new tissue coverage options for surgeons. For example, using the system of this invention, an abdominal defect of 10 centimeters can be closed in an average adult male (having a 36 inch waist) by only a 12% circumferencial contribution. The viscoelastic properties of skin are discussed in Wilhelmi, et al., *Creep v. Stretch: A Review of the Viscoelastic Properties of Skin,* 215 Annals of Plastic Surgery 41 (August 1998), which is incorporated by this reference.

This invention displays several critical advantages over existing systems. Human skin varies dramatically in elasticity and thickness depending on age and health. Unhealthy patients, such as oncology patients, often present with compounding maladies such as thin, friable and ischemic skin at retracted wounds from procedures, such as a mastectomy, where a retracted incision is further irritated by radiation, which significantly weakens the skin. In one embodiment of this invention, a variety of attachment structures match the tissue bonding strength to the required moving and stretching force to minimize necrosis and scaring. Additionally, various force distributing components may be used in a multitude of ways to create a broad range of moving and stretching forces that match the counter-tractive tensions on multiple planes present in various locations, and may vary in thickness and cross section to achieve a near infinite range of tension as required. Unlike some prior devices, an overhead beam is not required, and therefore this invention is capable of providing linear, radial, and circumferencial force exerted on multiple points.

Finally, this invention provides advances over current methods for moving and stretching plastic tissue through the introduction of gradual but unrelenting tension that is adjustable. A system according to this invention is virtually infinitely variable in stretching or closure force and can also be used in restricted areas where other skin closure systems would not fit, including under breasts, at the juncture of the neck and shoulder, and other such areas, and can be scaled up or down as required, using small attachment structures for ulcer closure and large attachment structures for abdominal closure, for example.

Systems of this invention allow rapid removal for dressing changes and uninterrupted visualization of the wound bed during routine cleaning procedures. When tension adjustment is required, it can be accomplished quickly, and the force applying components can include an easily read indicator. Thus, the nursing staff may replace wound dressings and readily reapply the force specified by the surgeon.

Utilizing dynamic force to move and stretch tissue offers the advantage of a relentless countertraction force, while allowing for expansion and contraction of the wound site, which greatly enhances patient mobility and is compliant with respiratory movements. In addition, an increased range of traction beyond the elasticity of the skin itself is provided. For example, a range of closure rates of 1.25 to 1.75 cm per day may be averaged over the course of treatment, which is considerably faster (about twice as fast) as the rates achieved using static counter traction methods of the prior art.

Accordingly, this invention is system of non-reactive components for moving and stretching plastic tissue that exerts a relatively constant dynamic force over a variety of distances and geometries, that is easily adjustable, and is self-adjusting.

DETAILED DESCRIPTION

I. Force Applying Components

Force applying components of this invention can integrate energy storage and force transmission, such as in an elastomeric rod, or can separate energy storage and transmission as in a spring connected to a cable.

A. Integrated Force Applying Components

An integrated force applying component according to this invention may be formed in rods, cords, bands, loops, sheets, nets, wires, strands, cables, tubes or other suitable structure. In one embodiment, the fac is an elastic tube that flattens out at the point of maximum load and becomes load dissipating. This tubular force applying component may be adapted to slide over the end of a trocar, allowing the force applying component to be driven through the tissue. For example, a force applying component may be driven through the wound edge using a trocar to prevent eversion. In an alternative embodiment, a rod-shaped force applying component is driven through the tissue using a needle swaged on to the rod-shaped fac. In yet another alternative embodiment, the force applying component is a belt having apertures adapted to capture a structure of the tissue attachment structure.

Figure 1:
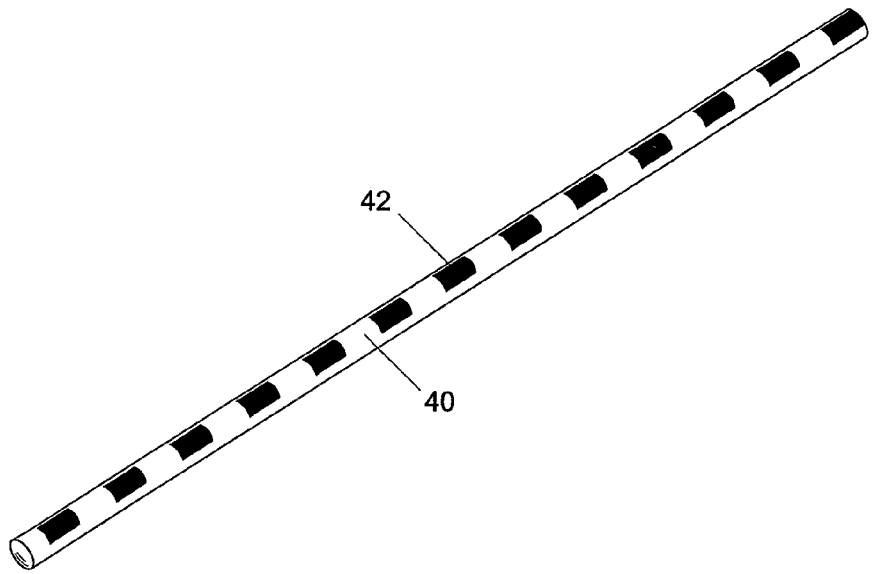
FIG. 1 is a perspective view of an efac according to one embodiment of this invention.

Force applying components ("facs") of this invention may have elastic properties ("efacs") and may be made from any suitable elastomeric material, including, without limitation, latex rubber, silicone, natural rubber and materials of similar elasticity, GR-S, neoprene, nitrile-butyl-polysulfide, ethylene-polyurethane, polyurethane, or any other suitable material that exhibits the property of exerting a return force when held in an elongated state at pressures and distances that are useful in the context of this invention. Efacs may provide a dynamic opposing force equal to or greater than the naturally occurring elastomeric traction forces of the tissue. The efacs of this invention generally are not endless loops but rather are lengths of a single strand, sometimes called a "monostrand," and may be either solid or hollow. In some instances, multiple strands or endless loops or bands may be used. Significantly, the efacs used in practicing this invention may be secured to a tissue attachment structure at virtually any point along the efac, providing variable tension within the elastic limits of the elastomer used. Use of a non-reactive fac is generally desirable. Non-reactive facs include components that are either immunologically inert or hypoallergenic, such a elastomers formed from silicone or a hypoallergenic form of latex rubber. An efac 40 is illustrated in FIG. 1 and shown attached to anchors in several of the other Figures.

Elastomers having various durometers may be used for the force applying components of this invention. In one embodiment, an efac has a 0.125 inch diameter with a nominal durometer of 40. Other efacs, such as efacs having a smaller diameter, may also be provided and differentiated one from another based on color. Alternative shapes, sizes and strengths may be appropriate in some situations. An extruded silicone efac may have a durometer of 40 (which allows a 5:1 stretch ratio). A molded silicone efac may have a durometer of 5 (which allows a 12:1 stretch ratio). In one embodiment, a tubing efac has a 0.625 inch internal diameter, a 0.125 inch external diameter and a Poisson ratio (the ratio of the transverse strain to the longitudinal strain) and durometer that provide a secure mechanical lock when sleeved over a structure having an outside diameter less than the internal diameter of the efac when the efac is compressed longitudinally, but greater than the internal diameter of the efac under longitudinal tension, and placed over the structure a distance equal to or greater than two times the outside diameter of the structure. These inherent qualities makes it easy to slide the end of this efac onto a trocar and yet lock in position under tension. Conversely, a secure mechanical lock may also be achieved by restraining the efac within a constricting aperture of a size greater than the tensioned diameter but less than the untensioned diameter, such that the untensioned end of the elastomer acts as a restraint upon the aperture.

Force applying components can include marks indicating tension or stretch such as the marks 42 printed as an interrupted line on efac 40, shown in the Figures. The indicia may be formed from colorant, including any means for providing visual contrast, such as ink, dye, paint, or the like. Force applying components may also be disposable. Force applying components can also be conventional springs made of metal or other materials like plastics.

In an alternative embodiment of this invention, the force applying component may be coupled to a force transmitting component that is relatively inelastic such as relatively inelastic cord, thread or other suitable structure. Such relatively inelastic force transmitting components may be used with both efacs and other facs, such as conventional coiled plastic or metal springs, as described immediately below.

B. Two Element Force Applying Components

Figure 2:
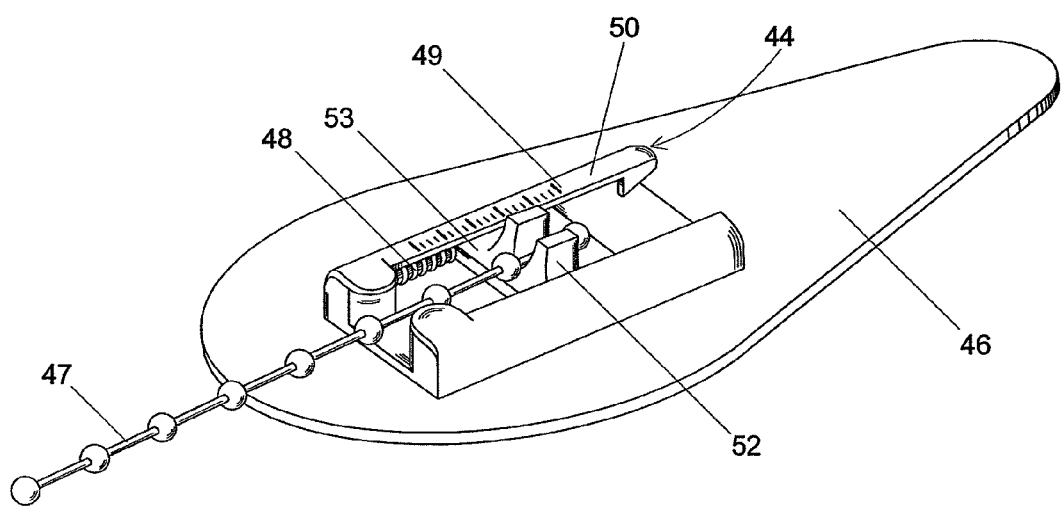
FIG. 2 is a perspective view of a fac and anchor system according to an embodiment of this invention.
Figure 3:
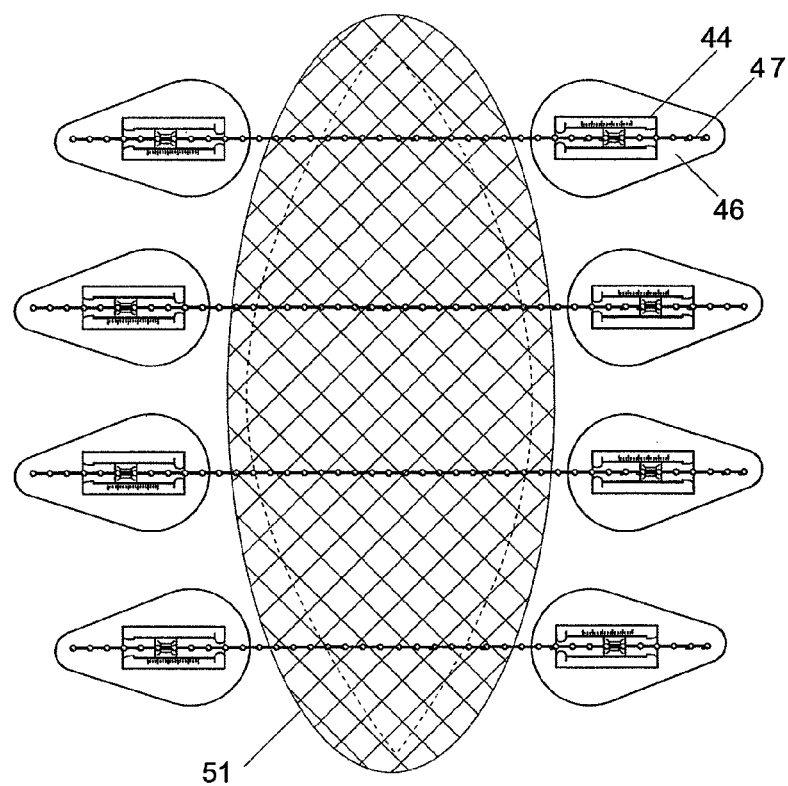
FIG. 3 is a top view of a group of facs and anchors of the type depicted in FIG. 2 positioned to close a wound shown schematically.

In an alternative embodiment shown in FIGS. 2 and 3, the force applying device 44 is attached to adhesive base 46. Alternatively, the base 46 may be secured to the tissue using a mechanical interface such as a staple or suture. Device 44 includes an internal biasing mechanism, such as a spring 48, capable of exerting a dynamic force between the body 50 of the device and slider 53 that has attachment structure 52 including slot 54 for capturing a nonelastic band 47, cable, cord, monofilament, tube, chain or other material used to bridge, encircle or engage the wound or wound margin. Anchor 44 may also include a force indicator 49, which reflects the amount of force exerted by reference to the position of slider 53. Anchor 44 may capture a non-elastic force applying component 47 yet still provide dynamic force to the tissue. In one embodiment, body 50 and slider 53 are formed from injection molded plastic. Pairs of anchors 44 may oppose each other across the wound, as illustrated in FIG. 3, and a dynamic closure force may be created by shortening the attachment cord 47 and drawing the devices 44 together, thereby compassing the internal springs 48, which devices 44 exert a constant force and are attached to the tissue beyond the wound margin 51.

II. Anchors

Anchors are used to transmit force to the tissue to be moved or stretched, and generally couple the force applying component to the tissue by providing (a) structure for coupling to the facs and (b) structure for coupling to the tissue.

A. Efacs Attachment Structures

As noted above, it is generally desirable to use a non-reactive elastomeric force applying component, such as a silicone, which is difficult to secure. The viscoplastic properties of low durometer material, such as silicone, fall below the threshold where the material will hold a knot. Adequate constricting force may not be applied upon the material by the material itself to retain it under load because the application of the load reduces the material diameter beyond the minimum compression diameter of the constricting loop. This precludes the use of conventional surgical knot tying techniques because such knots will not hold. An additional complication is the tendency of the material to creep, or slip, when alternative capture methods are used. Thus, it is difficult to secure a silicone efac when a force is applied to the efac without the efac being cut or otherwise caused to fail by the securing structure.

Successful structures for securing a silicone elastomer (or other low durometer material) must clamp the silicone elastomer structure with enough force to hold it in place (avoiding creep) but with sufficiently distributed force that the elastomer is not severed. This invention provides structures that result in sufficient contact between an efac (including a silicone efac) and anchor structure that the two do not slide relative to each other while avoiding cutting or tearing the efac. Such structure can be provided by squeezing the efac between, or forcing it against, planar or relatively large radius arcuate surfaces while avoiding contact between the efac and arises (intersections of planar surfaces) that might cut the elastomer.

Such a structure can be achieved with opposed planar or arcuate surfaces forming a Vee-shape and oriented so that tension on the efac forced into the gap between the surfaces will cause any reduction in outer diameter of the efac, such as occurs with added load, to result in the efac securing purchase lower in the Vee. In this manner, the efac-to-anchor structure contact is maintained, thereby improving the lock between the elastomer and anchor structure. Similarly, parallel surfaces may be engineered to provide an entrapment force and prescribed release tension for the efac in order to provide a maximum applicable tension and integral safety release.

The opposed surfaces can be provided by a variety of structures, such as arcuate surfaces provided by suitably rigid round wire or rod or by rounded opposed edges of plates of metal, plastic or other suitable material. Such structure can also be provided in other forms. For instance, the opposed surfaces between which the efac is trapped can also be provided by opposed flanges, typically positioned on a post or column and shaped so that the opposed flange surfaces get progressively closer together at points nearer the column. In such a structure, a first one of the opposed surfaces can be planar and can be, for instance, a flat base, provided that the other flange or other efac contact structure provides a surface that gets progressively closer to the first surface as the efac moves in the direction force applied to it during use will cause it to tend to move. For instance, the other flange can present a truncated conical surface.

Figure 4:
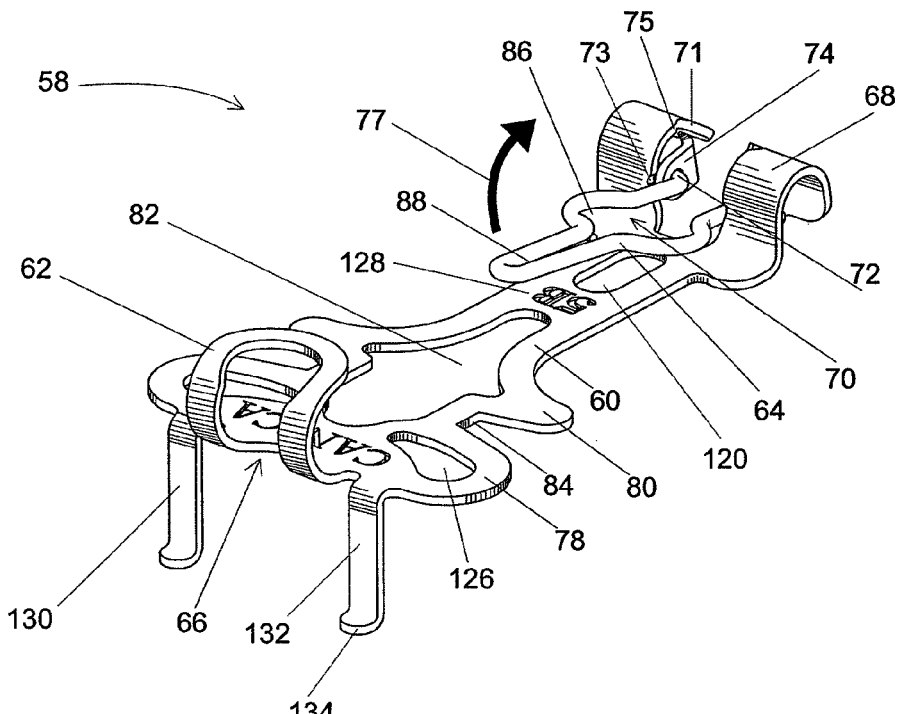
FIG. 4 is a perspective view of an anchor according to another embodiment of this invention.
Figure 5:
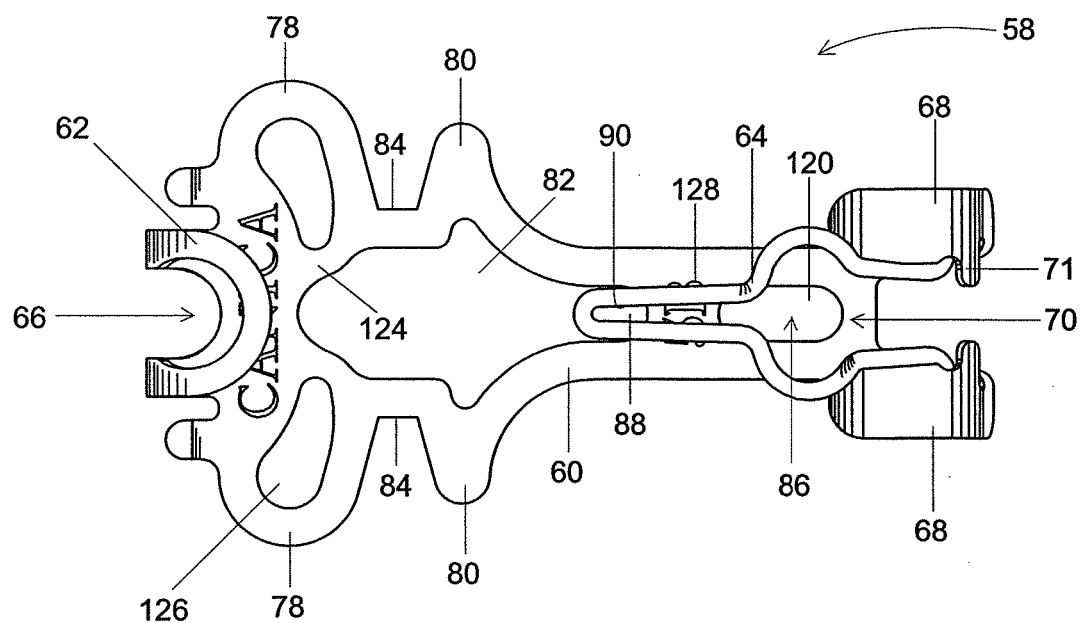
FIG. 5 is top view of the anchor of FIG. 4.

In the locking wire efac securing structures illustrated in FIGS. 4-7, fluke-bearing tissue anchor 58, shown in detail in FIGS. 4 and 5, has a generally flat body 60 that lies against skin or other tissue, a hook 62 around which a force applying component may be positioned, and a locking wire 64, to which an efac may be engaged. Hook 62 of anchor 58 is perforated by eye 66, through which an efac may optionally pass. Locking wire 64 extends from fenders 68 and includes keyhole shaped aperture 70. Locking wire 64 is capable of rotating, as shown by arrow 77 in FIG. 4. Projections 71 extend inward from each fender 68, limiting rotation of locking wire 64. Fenders 68 protect surrounding tissue from locking wire arms 72 and from tabs 74. Each tab 74 includes an aperture adapted to receive arms 72 of locking wire 64. The opposed edges of fenders 68 contact arms 72 and are closer together between detents 73 and 75 so that locking wire 64 prefers one of two positions: down, as shown in FIG. 4, or up, as indicated by arrow 77. In one embodiment, locking wire 64 is tensioned steel so that arms 72 are retained in tabs 74 by the spring tension. In alternative embodiments, the locking wire is formed as a staple. Hips 78 and wings 80 extend outwardly from the body 60 and from the center opening 82. Indents 84 hide tabs that result from manufacturing the anchors from sheet metal.

Figure 6:
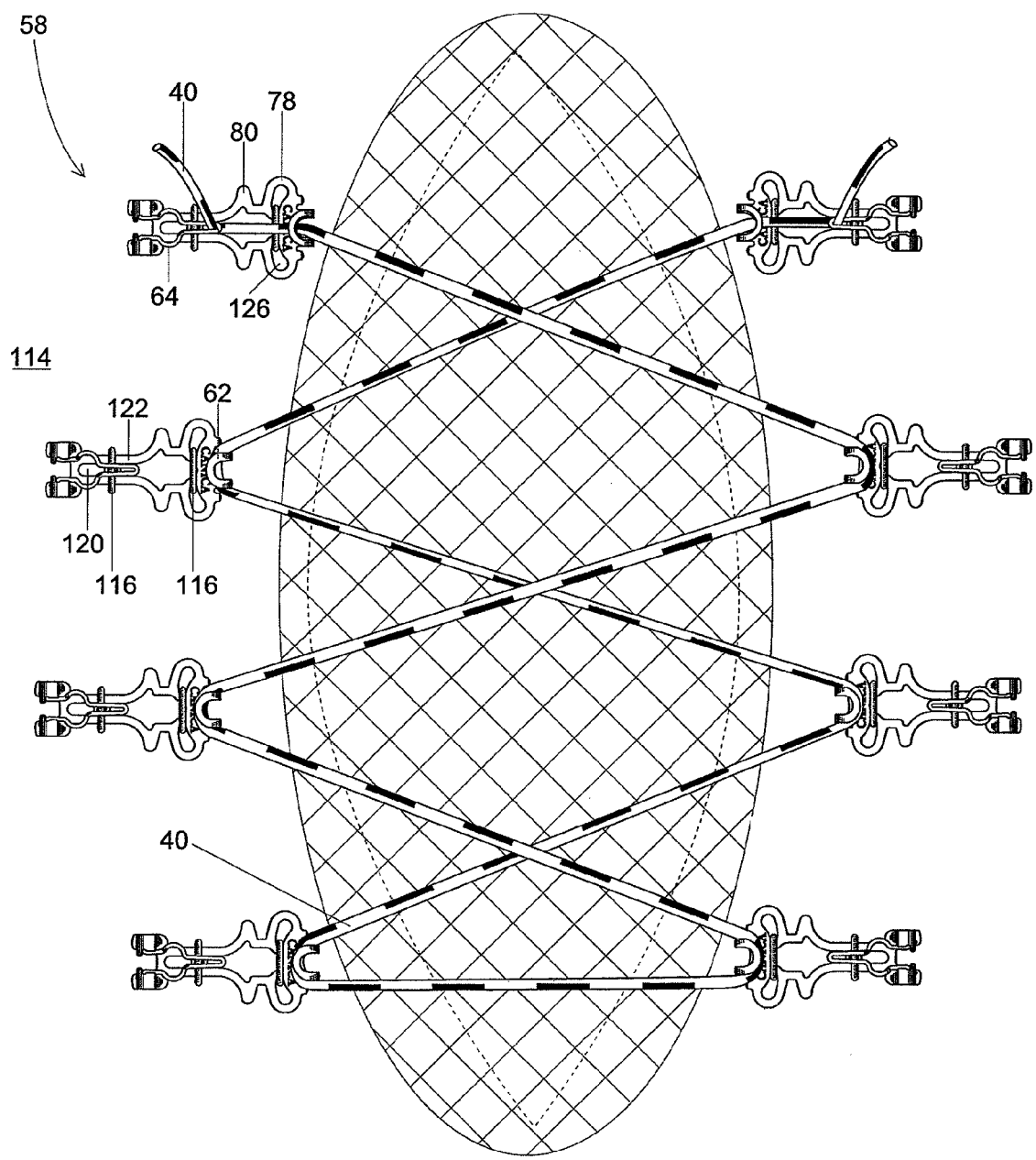
FIG. 6 is a top view of a group of anchors as depicted in FIG. 4 among which an efac as depicted in FIG. 1 has been laced across a wound shown schematically.
Figure 7:
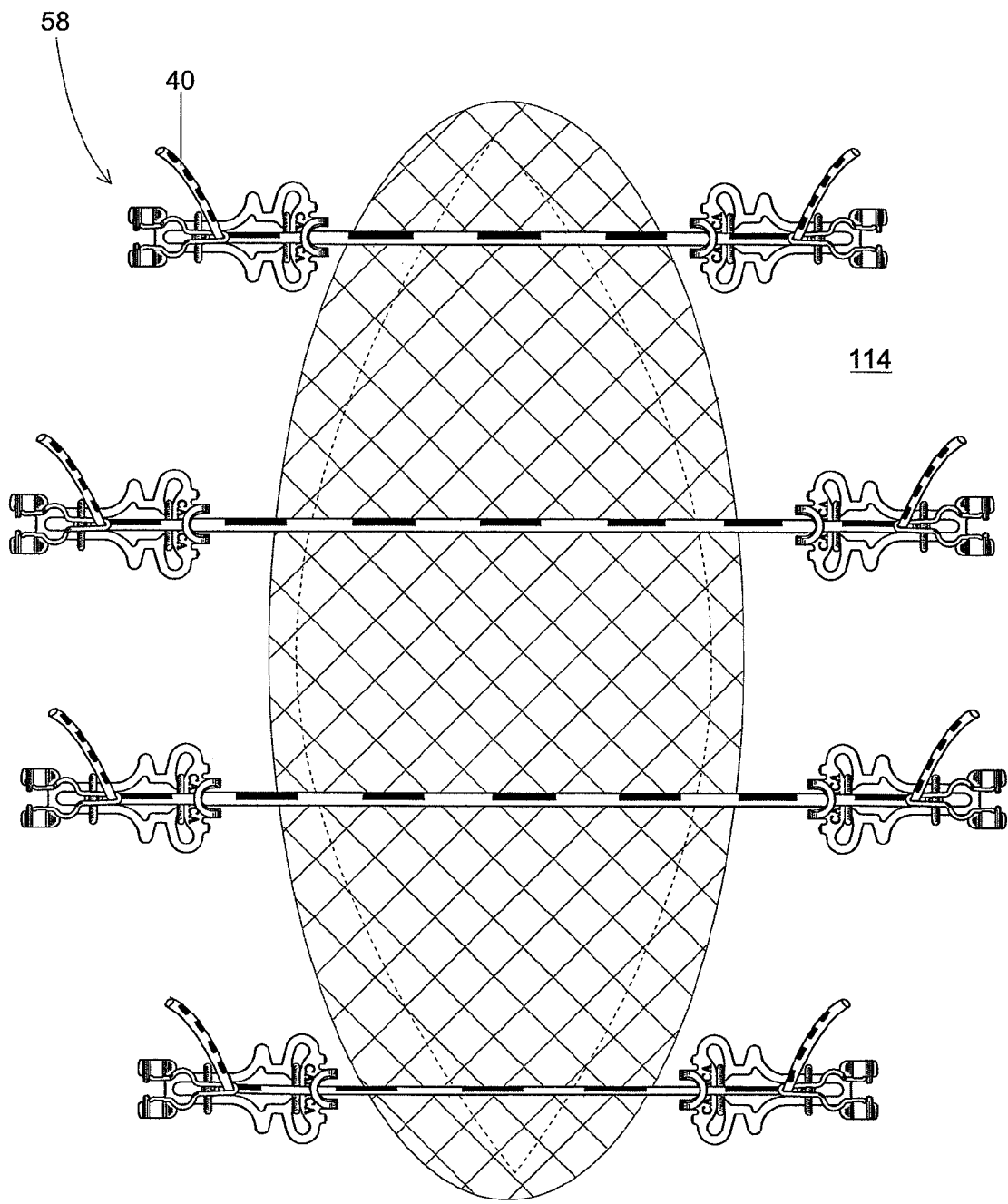
FIG. 7 is a top view of the system of FIG. 6 according to an alternative installation method.

An efac 40 may be retained by locking wire 64, as illustrated in FIGS. 6 and 7. Larger opening 86 of keyhole aperture 70 receives efac 40, which is compressed and locked into the smaller elastomer-wedging section 88 of aperture 70, as shown in FIG. 6. Wire 64 is round, presenting arcuate surfaces 90. Efac 40 may be retained by locking wire 64 either by passing first through eye 66 of hook 62 or from a subcutaneous presentation through the center opening 82 of anchor 58. Alternatively, the locking wire 64 may be formed in any shape that provides parallel or converging surfaces that entrap the efac.

Figure 9:
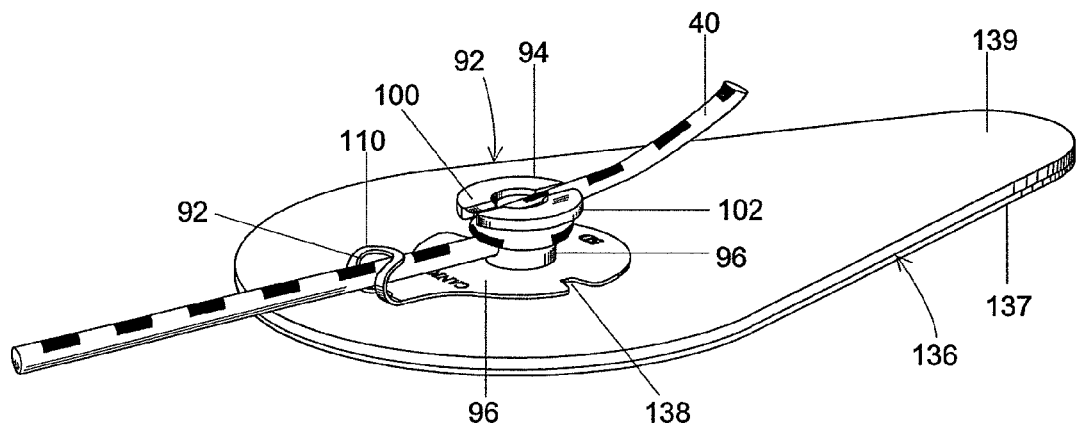
FIG. 9 is a perspective view of another alternative anchor of this invention together with the efac of FIG. 1.
Figure 10:
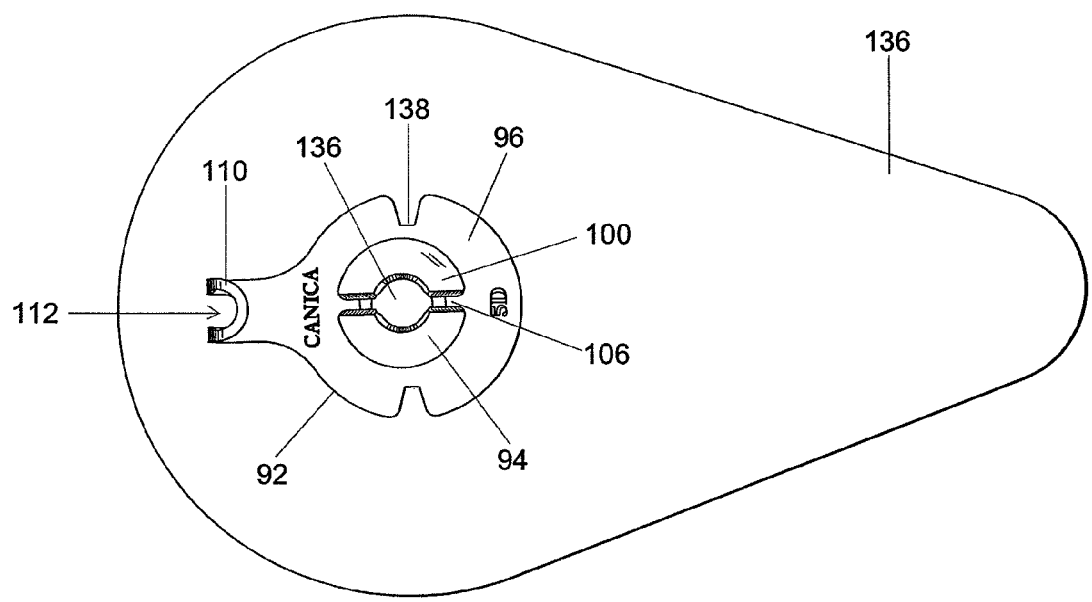
FIG. 10 is a top view of the anchor of FIG. 9.
Figure 11:
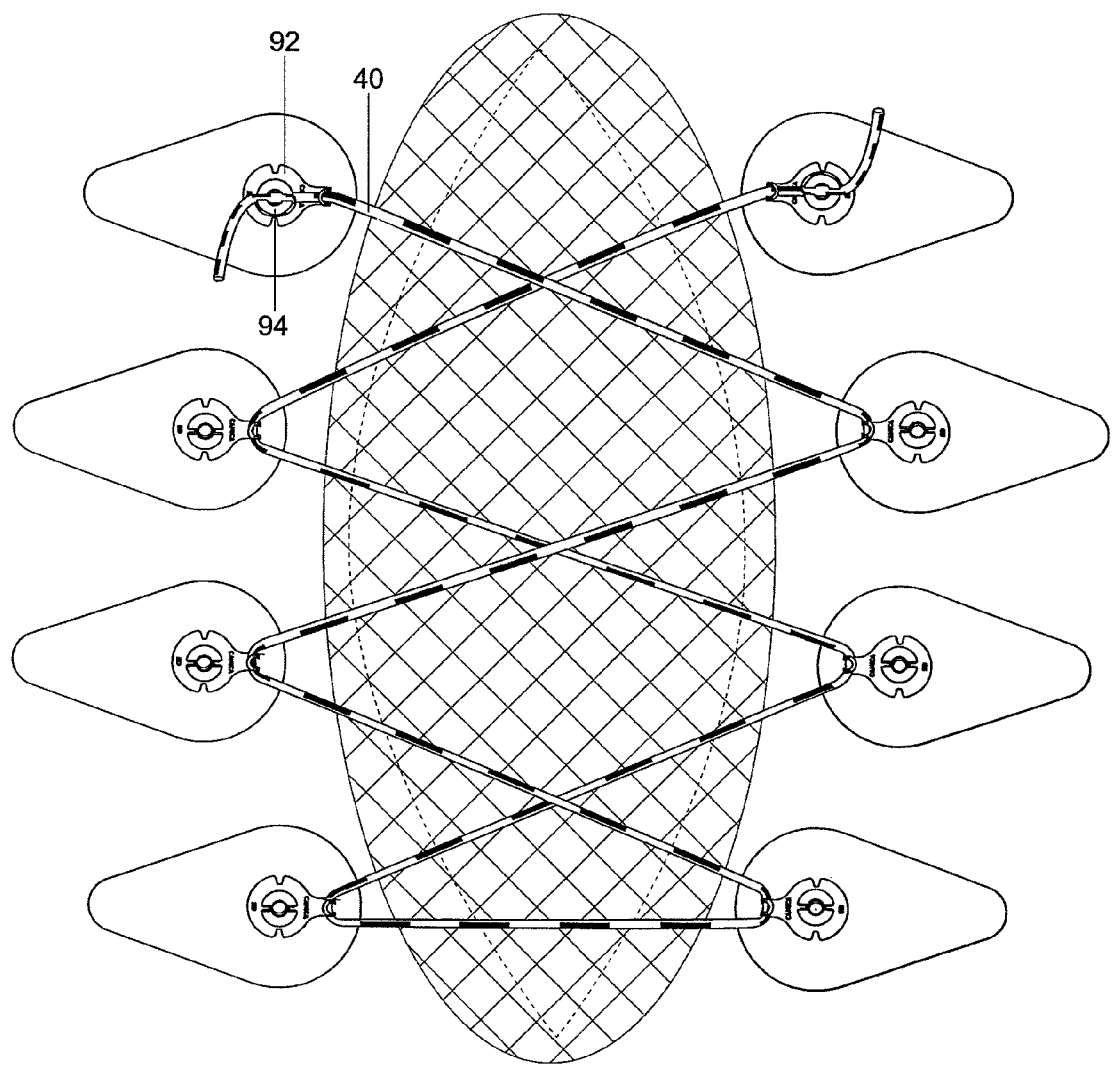
FIG. 11 is a top view of a system according to another embodiment of this invention.

In an alternative embodiment, a locking rivet efac securing structure, illustrated in FIGS. 9-11 as anchor 92, includes rivet 94 that extends from the body 96 and includes a post 98 and a cap 100. Cap 100 includes rim 102 and conical sections 104 (visible in rivet 156 in FIG. 12). Slot 106, which extends through cap 100 and partially into post 98 so that post 98 is split by slot 106, is adapted to receive an efac 40, which may also be wrapped around at least part of post 98, as illustrated in FIG. 9. The efac 40 thus contacts a substantial portion of the anchor surfaces by passing first through slot 106 in post 98 and then wrapping around a significant portion of the circumference of the post 98. Wrapping the efac 40 around, in effect, a 90° corner as the efac 40 exits the slot 106 causes the efac 40 to flatten at the corner, establishing substantial surface contact between the efac 40 and the anchor 92, thereby resisting slippage between the two. Efac 40 may also wrap around a second corner and pass through slot 106 in post 98 a second time, securing efac 40 in position. Anchor 92 also includes a hook 110 around which an efac may be positioned. Hook 110 is perforated by eye 112, through which an efac 40 may optionally pass.

Various arcuate or curved surface shapes for anchor efacs attachment structures are described above. It should be understood that functionally equivalent shapes can also be used, such as, for instance, a rod having a cross-section that is not curved but rather is a polygon.

B. Tissue Attachment Structures

Anchors of this invention attach to the tissue either non-invasively using an adhesive or invasively, using flukes, staples, sutures and, optionally, adhesive. Depending on the nature and location of the wound, engagement between an attachment structure and the tissue may occur in different ways. Specifically, it is sometimes necessary (and or desirable) to attach only to the surface of exposed skin. Other times it is necessary to engage the skin at least in part with structures that penetrate the skin's surface, or to engage relatively deep tissue so that force is applied not only to the superficial tissue (skin) but also to some of the underlying tissue (fascia).

i. Invasive Tissue Attachment Structures

In one "invasive" embodiment of this invention, the tissue attachment structure is an anchor that includes flukes for engaging the tissue and that may also be secured to the tissue using sutures or staples. In another invasive embodiment, the anchor is flukeless and may be attached using staples, sutures, any suitable adhesive or any combination thereof.

Fluke-bearing tissue anchor 58, shown in FIGS. 4-7, provides a relatively wide area of contact with tissue, such as skin 114, allowing maximum levels of counter-traction to be applied while minimizing localized tissue failures. Wings 80 enhance the stability of the anchor body 60. Fluke-bearing tissue anchor 58 may also be attached to skin 114 with at least one staple 116, or by sutures 118, which may pass at least partially through and on one or both sides of slot 120 and around one or both of hips 78 or by surgical skin glue, or other adhesive. Staples may be installed across travel way 122, across center section 124, or across one or both hips 78. One staple may be installed across travel way 122 and a second staple across center section 124. Alternatively, one staple may be installed across travel way 122 and two additional staples installed, one on each hip 78. Staples may be installed using a surgical stapler, while slot 120, hip openings 126 and center opening 82 provide access to the staples for ease of removal.

Wings 80 stop movement of staple 116 at an end of travel way 122 that extends between wings 80 and indicia 128. Indicia 128 may be a half thickness etch mark used both for part identification and as a visual target by the surgeon for locating the position of the rear staple. Indicia 128 may be chemically milled onto body 60 or may be applied in any other suitable manner. Travel way 122 provides staple 116 unrestricted travel, allowing for the skin contribution (stretch in the tissue occurring between the flukes and the rear of the anchor) and differential stretch between flukes 130 and anchor body 60 that would occur in skin located directly under anchor body 60. Securing the anchor with a staple in this manner counteracts the tip-up force under high load at high stress traction point. Travel way 122 allows body 60 of anchor 58 to slide in a direction roughly perpendicular to the wound, but holds anchor 58 firmly against skin 114. Movement of the anchor 58 in this manner prevents flukes 130 from digging into the subdermal layers of the skin, which can result form high counter-traction loads presenting off-axis thrust beyond the anti-torque forces provided by the tissue.

A marking instrument may be used to mark the tissue prior to attachment of anchor 58. Insertion of prongs or flukes 130 having legs 132 and feet 134 into and penetrating the dermal layers of skin 114 holds fluke-bearing tissue anchor 58 firmly in place. Thus, flukes 130 act as grapples, engaging skin 114 because of their shape and angle, and remaining engaged under tension. Feet 134 aid in this grappling function, preventing fluke-bearing anchor 58 from popping out of the skin, and serve as a safety feature, preventing flukes 130 from being driven further into the tissue if direct pressure is applied to anchor 58. Flukes 130 may be disengaged from skin 114 by releasing the tension exerted by efac 40 and withdrawing flukes 130 at an angle opposite to the angle of engagement.

Flukes 130, shown in the drawings, are merely illustrative, and the flukes may have other cross sectional and longitudinal shapes and could conceivably be bent in the process of installation. As an example, one variation of flukes 130 could have wider and longer legs and feet. Flukes 130 could be round rather than square or rectangular in cross section. In another embodiment, the anchor incorporates the staple function so that the anchor includes prongs that bend and capture the skin similar to the prongs on a staple. In this manner, the anchor would function as both an anchor and a staple.

ii. Non-Invasive Tissue Attachment Structures

As an alternative to more invasive structures and techniques, tissue attachment structure of the invention may be attached to the tissue using suitable adhesive. In one such embodiment, the tissue attachment structure is an adhesive-backed, generally planar portion of an anchor having structure for securing a force applying component. The planar portion may be a thin stainless steel "coin" bearing suitable adhesive, providing a peel-off, stick-on-skin anchor that secures the anchor to the tissue. Adhesive anchors may be provided in a variety of shapes and sizes.

The adhesive may be a hydrocolloid adhesive membrane that atraumatically grips skin or other tissue. For example, aggressive high tack adhesives may be combined with hydrocolloid gel to create a skin seal that may reside on skin or other tissue for extended periods without complication or compromise to the health of the tissue. In addition, the viscous properties of the gel minimize the shear load on the adhesive. In this manner, the hydrocolloid synchronizes to the stretch of the skin and thereby minimizes the sheer force on the adhesive.

Anchor 92, shown in detail in FIGS. 9 and 10, has a generally flat body 96 that is laminated to a hydrocolloid adhesive base 136 so that it lies against the skin or other tissue. Base 136 includes adhesive 137 attached to base sheet 139, which may be a non-woven fabric, a plastic film, sheet metal, or any other appropriate material. Body 96 of anchor 92 includes cutouts 138, allowing maximum surface area for lamination to the adhesive base 136, and providing adequate stability to alleviate the tendency for the anchor to tip forward under load within the intended working load limits. Anchor 92 also includes a hook 110 around which an efac may be positioned, and a rivet 94, to which an efac may be secured as described above. Anchor 92 may also include an opening 144, which extends through post 98, cap 100 and base 136 and which is adapted to receive an efac.

Adhesive anchor 92 shown in FIGS. 9-11 has an adhesive base in the shape of a teardrop, which allows positioning of a large number of anchors along a wound edge, while distributing the applied load over the largest possible area of healthy skin. A teardrop shape also allows anchors to be placed close together on the inside of a curve. In an alternative embodiment, such as the anchor 146 in FIG. 8, the adhesive base 147 is circular. Any other suitable shape may also be used.

Figure 8:
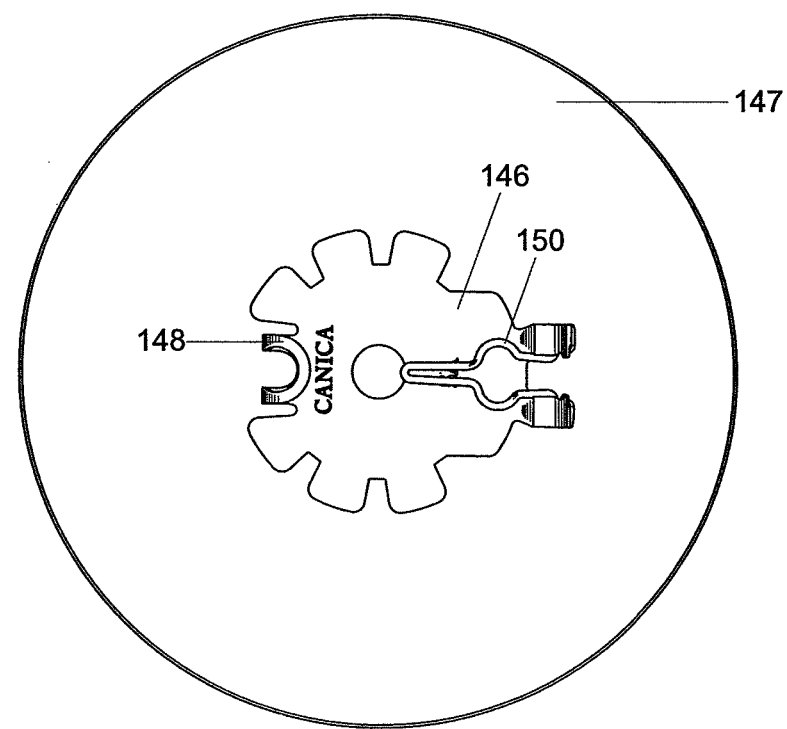
FIG. 8 is a top view of an anchor according to an alternative embodiment of this invention.

As FIG. 8 also illustrates, an anchor having a locking wire and hook may also be attached to an adhesive base, so that the locking wire secures a force applying component as described above. As is shown in FIG. 8, anchor 146 includes a hook 148 and locking wire 150 as described above.

Figure 12:
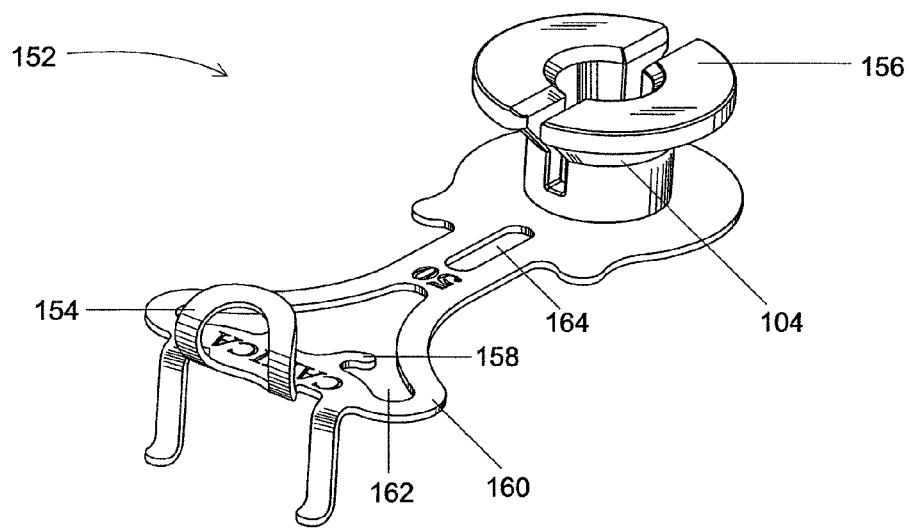
FIG. 12 is a perspective view of an anchor according to an alternative embodiment of this invention.

In another embodiment, a fluke bearing anchor includes a locking rivet and hook, and secures efac as described above. For example, as shown in FIG. 12, fluked anchor 152 includes a hook 154 and locking rivet 156 as described above. Ears 158 extend from hips 160 into opening 162, forward of locking rivet 156 and slot 164. Ears 158 form a staple landing for further stabilization of the forward portion of the anchor, if required.

Figure 13:
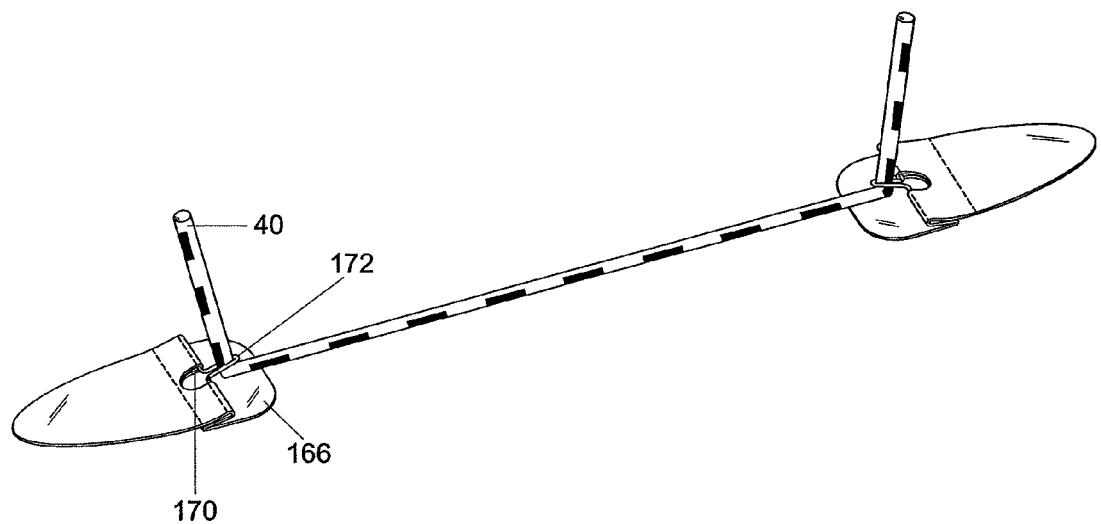
FIG. 13 is a perspective view of a system according to another embodiment of this invention.

In another alternative embodiment, shown in FIG. 13, a woven or non-woven, textile tape 166 with an aggressive skin adhesive is folded to entrap a wire bar that protrudes through a hole 170 in the tape, forming a locking wire 172 that functions to secure an efac as described above. The tape 166 may be applied to the tissue and left for several weeks. In the configuration of components of this system shown in FIG. 13, at least two such devices are taped on opposing sides of a wound and may engage a tensioned efac.

In yet another embodiment of this invention, a force applying component may be directly attached to an adhesive using an adhesive. For example, a silicone elastomer structure may be designed having adhesive end portions for adhering to skin or other tissue, so that each adhesive end portion is the tissue attachment structure.

Any of the other anchors described and illustrated herein may be fabricated from metal, plastic or other suitable materials. For instance, the anchors may be made from sheet or coil metal and formed by punching, stamping, fine blanking, rolling or chemical milling. An anchor may be chemically milled, using a tab-less free etching process, and the logo and identifier marks may be half etched in a single process. The photo resist mask is chemically stripped and the anchor is tumbled in abrasive media for fine de-burring before final passivation, cleaning and processing. Anchors of this invention may be manufactured by turning on a screw machine, or by metal injection molding. All of the tissue attachment structure and anchor designs described herein may be produced in a variety of sizes.

In one embodiment of this invention, each pair of tissue attachment structures transmits a controlled dynamic stretching or closure force between about 0 and about 1000 grams of measured as measured in a static state. In an alternate embodiment, components of this invention are scaled down and exert lesser force, while another embodiment includes components on a larger scale and therefore exert a greater force. The anchors of this invention typically have a body length of about 5 mm to about 60 mm and a body width of about 2 mm to about 50 mm. The smallest anchors typically have a body width of about 2 mm to about 10 mm and a body length of about 5 mm to about 15 mm. Anchors for general surgical use typically have a body width of about 10 mm to about 25 mm and a body length of about 20 mm to about 30 mm. In a larger embodiment for treatment of abdominal defects, the anchors typically have a body width of about 20 mm to about 50 mm and a body length of about 25 mm to about 60 mm.

III. Force Distributing Structures

Certain embodiments of the invention include a force distributing structure. Use of a force distributing structure is advantageous because it evenly distributes the closure force, eliminates high stress points, minimizes discomfort and also minimizes localized skin failures, which is especially critical when skin health is compromised.

Force distributing structures can be either woven or non-woven engineered fabrics, monomer or polymer membranes, extruded or formed viscoelastic materials, or vulcanizing or solidifying materials having specific stretch characteristics. The force distribution structure can have inclusions to provide wound edge stability, and viscoelastic properties that range between non-elastic to a coefficient of elasticity equal to the elasticity found in healthy skin. In one embodiment, the force distributing material is bonded to hydrocolloid adhesive or any other suitable adhesive and then attached the tissue. Other attachment structures can also be used.

Pockets or tunnels can be woven or formed into the force distributing material in a repeating pattern. The tunnels may be of a fixed length, such as about ¾ of an inch, and may be located at the edge of the force distributing material. The tunnels allow engagement of a locking wire, providing a method of coupling the force distributing structure to the force applying component, as described above. The fabric may be designed to support a suture or staple if additional support is required for specific portions of the wound, and may be used to lift the wound edge with interrupted simple sutures to prevent the wound edges from everting.

The fabric dissipates the load over the fabric and transmits the load to the tissue very evenly, over a large area. In this embodiment, the fabric is designed to stretch at a rate equal to that which would be required to migrate severely retracted skin back to a state of elasticity.

In an alternative embodiment, the force distributing structure is a loop top fabric. The fabric includes a loop top, which allows hook type fasteners to engage the loops at any point. The fabric may also include a method of coupling the fabric to the force applying structure, such as a plastic rivet or a locking wire having a hooked base to engage the fabric loops.

IV. Systems

A. Surgical Systems

In applying a surgical system of this invention to a patient, the surgeon determines which direction the tissue needs to be moved. The wound length is measured in order to estimate the number of anchors required. The appropriate spacing of anchors will depend on the location and nature of the wound and other factors. A long wound on a human forearm might, for instance, use anchors that are placed about every three centimeters. A skin marker is used to draw a line from about one half to about one centimeter from the margin, or edge, of the wound. Anchors are then installed, generally starting at the center of the wound, and typically in opposing pairs. Either a marking instrument or the flukes of an anchor is used to provide guide marks to the surgeon for insertion of flukes 130 of anchor 58 into skin 114, and stab penetrations are made with a suitable blade, such as a #11 blade. Fluke-bearing anchor 58 is then stapled, sutured or glued to secure it in place upon the skin. If secured using at least one staple, a staple 116 is installed across travel way 122. Second and possibly a third staples may be installed if an increase in stabilization of the forward portion of anchor 58 is required. Using two staples provides maximum closure force and is frequently used in the treatment of severely retracted wounds. Installing three staples may be desirable to provide maximum load distribution in thin or damaged skin.

The wound bed is dressed with a either a wet, dry, or other suitable dressing in order to prevent the fac from directly contacting the open wound area. One such suitable dressing is Duoderm® dressing, available from Smith & Nephew, or Tegaderm® dressing, available from 3M. The anchors are then coupled to the force applying structure, which, in the embodiments shown in FIGS. 4-7, is a silicone elastomer 40. Efacs apply a relatively constant force over a relatively large distance. Efac 40 may be threaded through eye 66 of hook 62 of anchor 58, may pass around hook 62 of anchor 58 or may be gripped by locking wire. After passing the efac through the eye and wire, and pulling the efac to the desired tension, the wire clip is held down and the efac is pulled upward, locking the efac in place.

As illustrated in FIGS. 6 and 11, the efac 40 may be "laced" through a series of anchor hooks by passing around hooks of each anchor unit on the wound margin, or edge. Efac 40 may engage a locking wire (or a locking rivet) to terminate the lace end. The lacing installation method provides equal tension along the wound and facilitates quick dressing changes. This laced version is used when even amounts of tension are desired along a shear plane, such as is typically desired with a long, straight incision.

Figure 14:
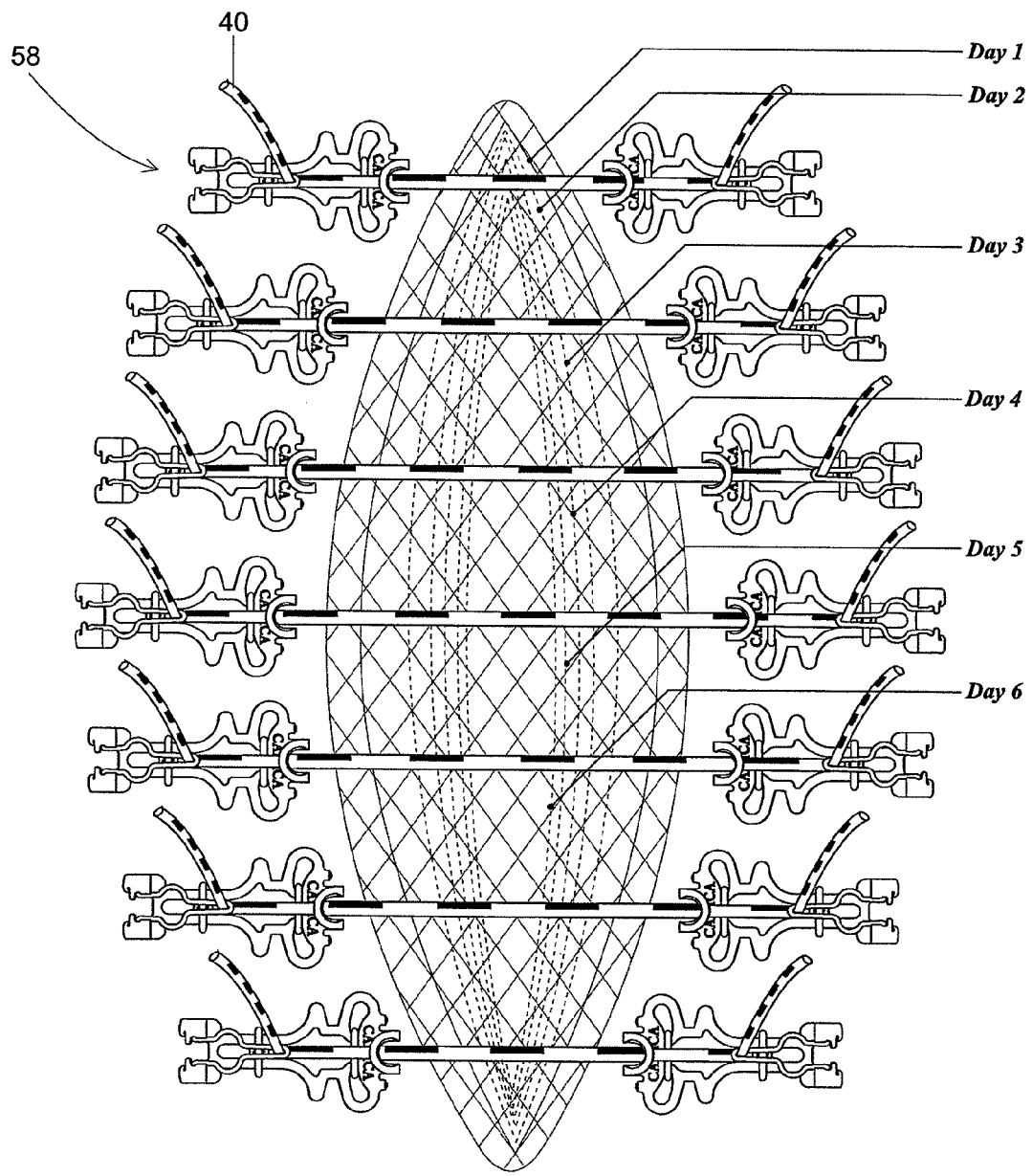
FIG. 14 is a top view similar to and using the same system shown in FIG. 7, showing a tissue healing pattern schematically.

As illustrated in FIGS. 7 and 14, efacs may be used with sets of paired anchors. Opposite ends of efac 40 are threaded through eye 66 of hook 62 of anchor 58 and then also gripped by locking wire 64. This method allows for the control of unbalanced wound tension and is desirable where different closure forces or alternate pull solutions are required. A length of efac between two opposed anchors is used individually or in multiples when an irregularly shaped defect requires varied forces along more than one thrust plane. This would be typical of a Z-plasty, an L-flap incision or an incision not on the transdermal plane. Additionally, the efac may wrap around the body part. A single efac may also be used to encircle an object or wound and create radial tension. In all installation methods, efacs may be unlaced or uncleated repeatedly to allow for easy dressing changes, re-positioning, and re-tensioning.

An example of wound closure progress using a point-to-point installation method as described above is illustrated in FIG. 14. External forces, such respiratory or ambulatory activity place various stress points on the wound. Adjusting elastomeric tensions, at dressing changes for example, allows a doctor to guide the healing pattern.

Figure 15:
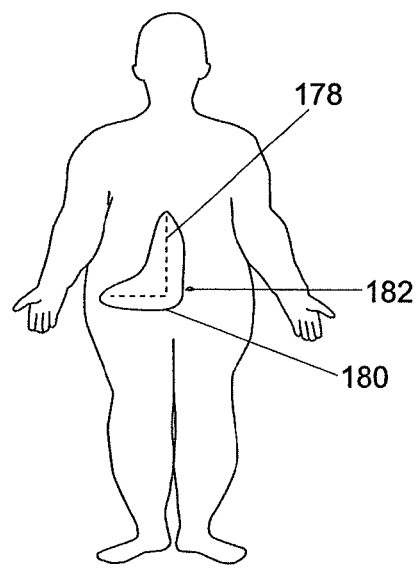
FIGS. 15-18 illustrate use of a system of this invention on a compound and non-linear incision.
Figure 16:
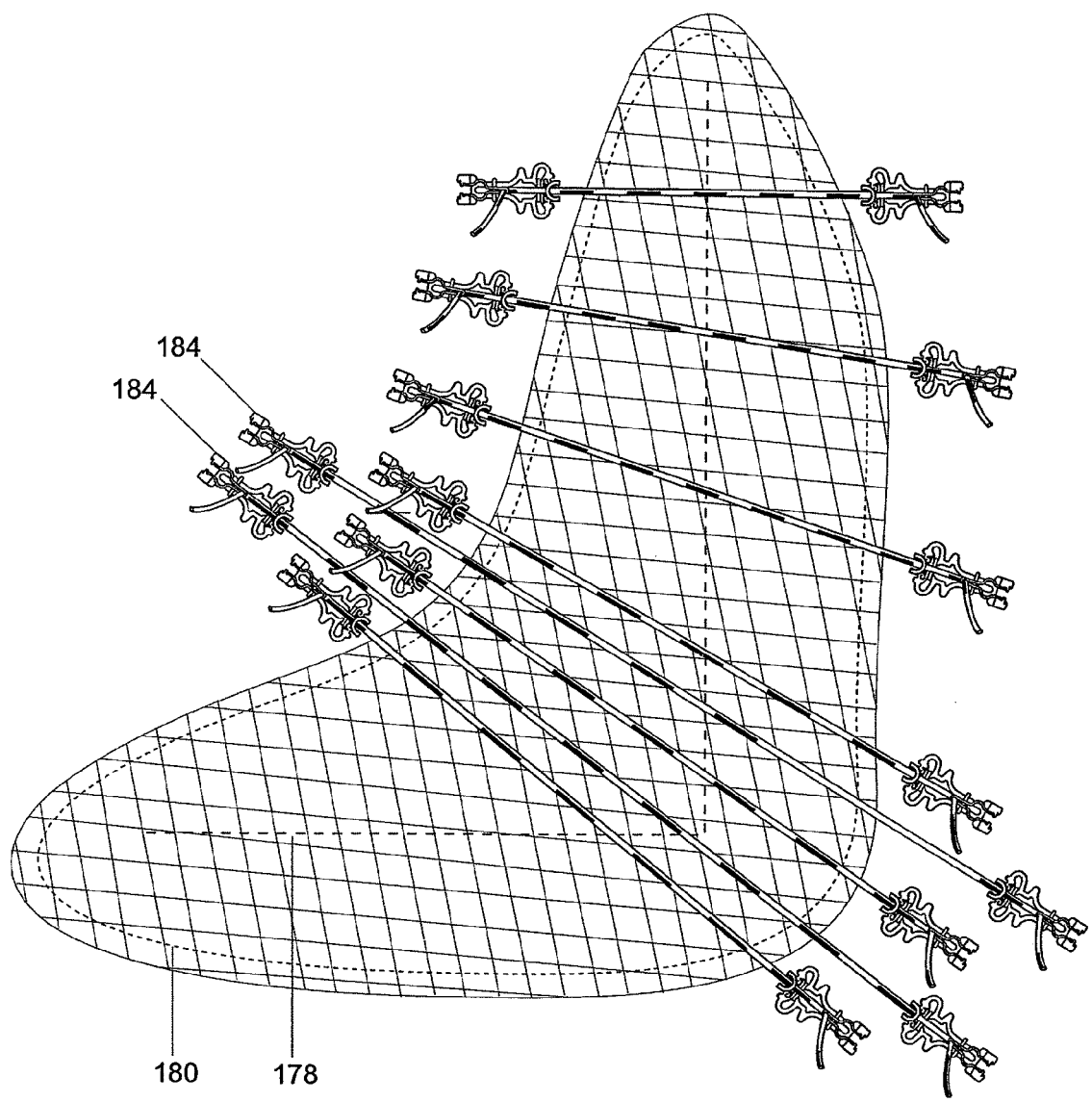
Figure 17:
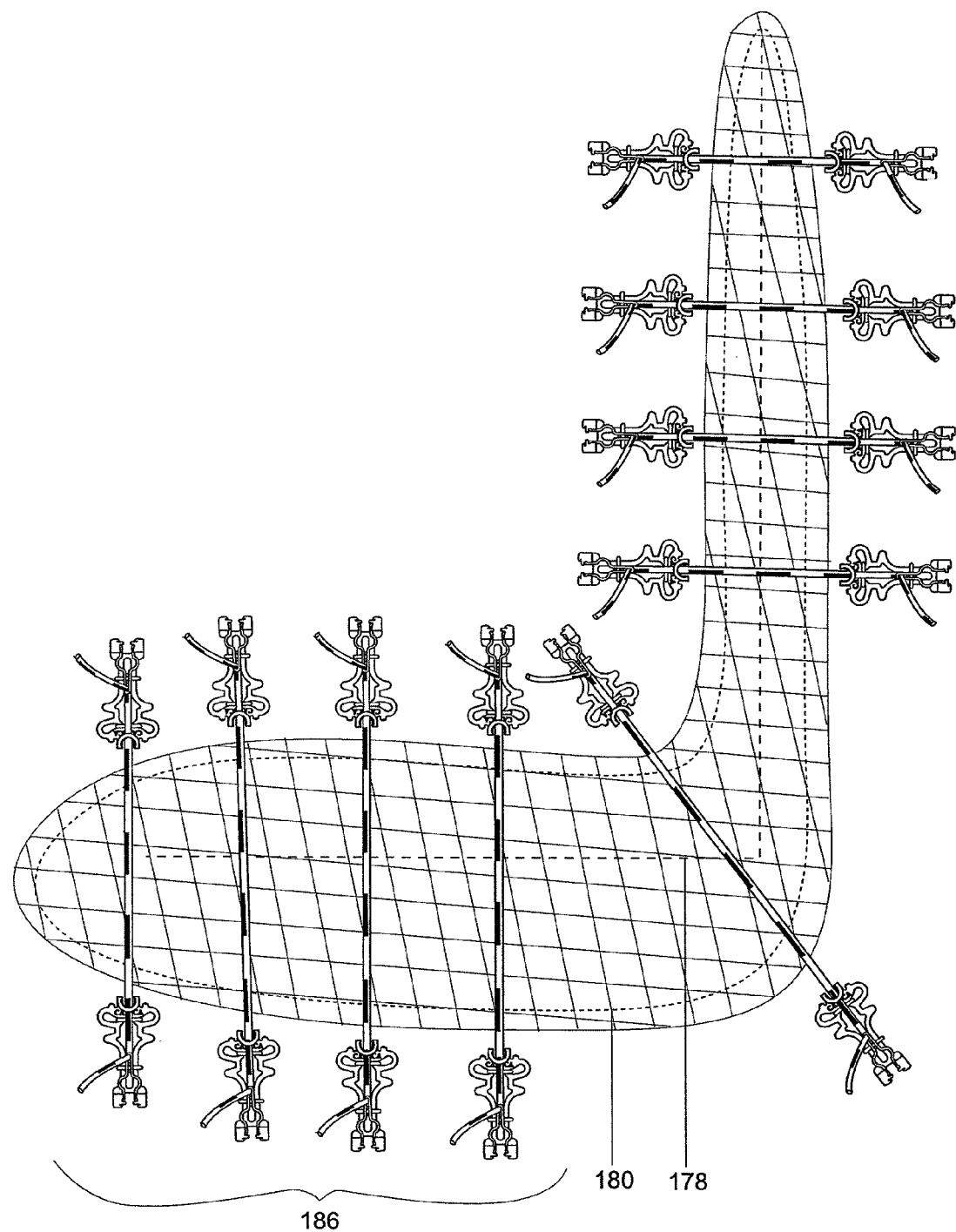
Figure 18:
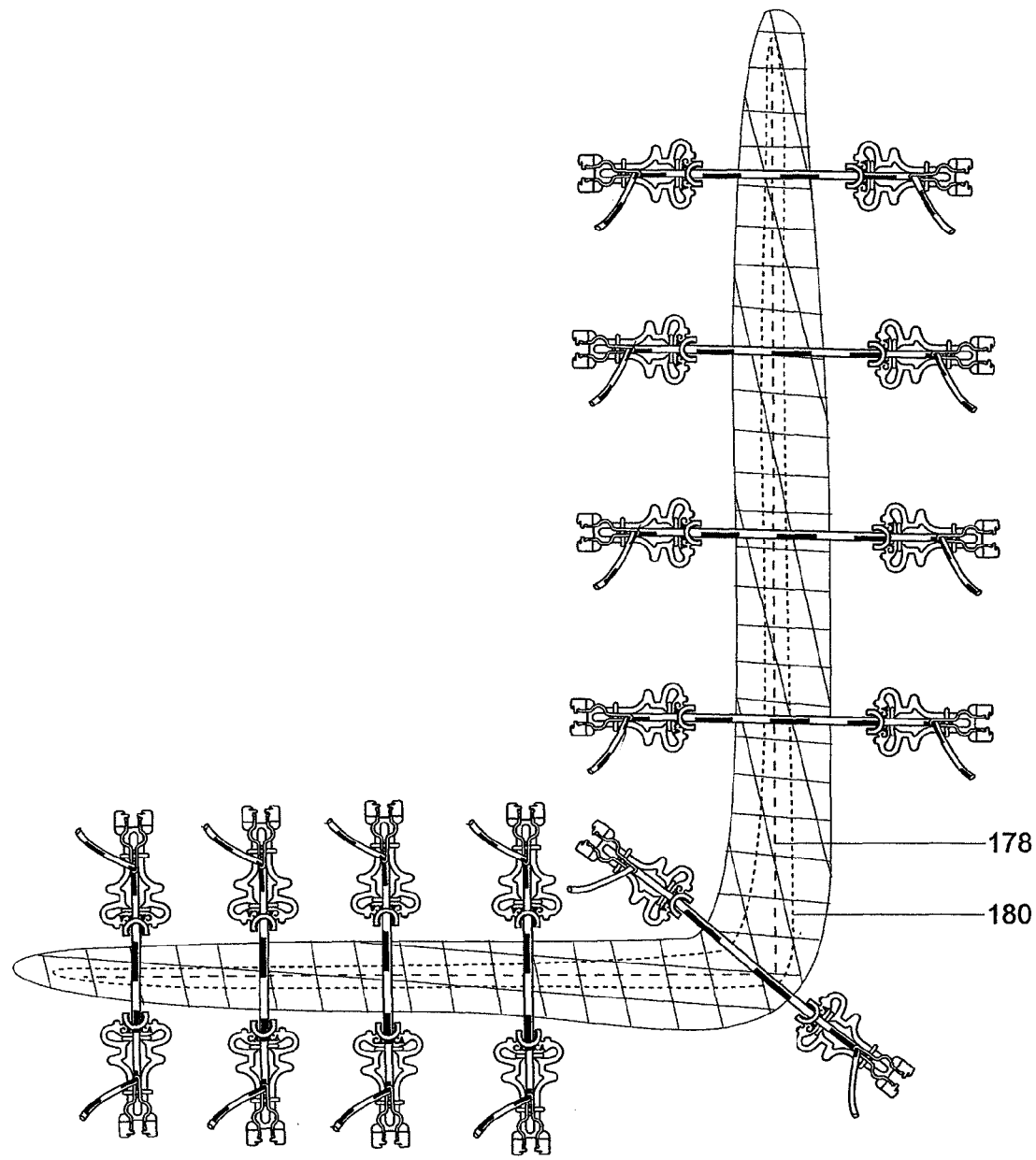

FIGS. 15-18 illustrate the use of a system of this invention to effect closure of a compound and non-linear incision, which, for example, may present closure difficulties as a retracted abdominal incision in an obese patient. FIG. 15 illustrates the process of mapping the original incision 178, and comparing it to the retracted wound area 180. By referencing a landmark, such as umbilicus 182, and comparing the wound area 180 to the original incision 178, the forces acting upon the wound may be identified, and a counter-retractive strategy may be formulated. FIG. 16 shows the first phase of reduction applied across the wound. In some cases, as shown in FIG. 16, a second row of anchors 184 may be used. The second phase of reduction, shown in FIG. 17, involves applying a lower set of anchors 186. FIG. 18 illustrates the third phase of reduction. Reduction of the wound is shown by comparing the wound 180 in the figures.

Figure 19:
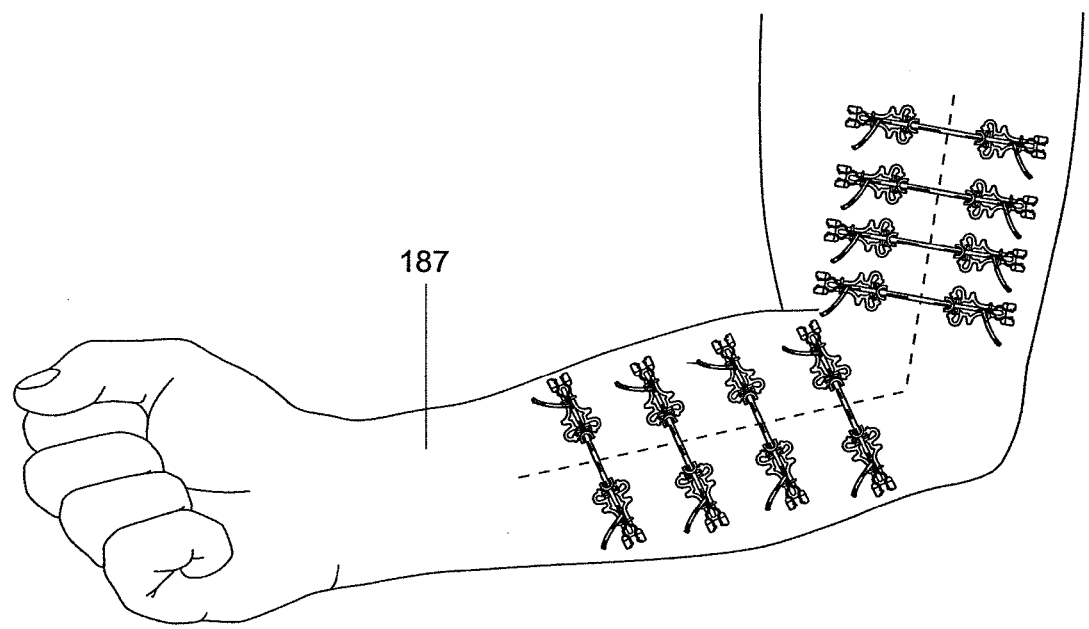
FIG. 19 illustrates use of a system of this invention to close a wound on an extremity.

FIG. 19 illustrates use of a system of this invention to close a wound of an extremity such as arm 187.

B. Clinical Systems

Atraumatic embodiments, such as embodiments utilizing hydrocolloid adhesive or flukeless anchors rather than sutures or staples, may be applied in a clinical setting by nursing staff, instead of doctors. For example, as shown in FIG. 9, an atraumatic system utilizing teardrop shaped hydrocolloid anchors 92 may be applied by attaching anchors along the length of the wound, in a manner similar to the method described for a surgical, or traumatic, embodiment. Force applying components are also applied as described above, either laced or connected by two opposing anchors.

C. Force Distributing Structure Systems

One system utilizes an engineered fabric having tunnels adapted to retain a formed wire anchor, which couples a force applying structure, such as a silicone elastomer, to an attachment structure, such as a fabric, which may be attached to the tissue using either adhesive, sutures or staples, so that this embodiment may be invasive or non-invasive. Another embodiment incorporating a force distributing structure, such as an engineered fabric, includes a strip fabric that also may be attached to the tissue using adhesive, sutures, or staples and that is coupled to a force applying structure, such as a silicone elastomer, with formed wire anchors that are fixed to the fabric either by stitching, weaving or direct mechanical means, such as staples or rivets, or are attached using adhesive. Yet another embodiment of a system using a force distributing structure includes an engineered fabric having a loop top, which fabric may be attached to the tissue using adhesive, sutures, or staples. This loop top fabric is attached to a force applying structure. The force applying structure may be a silicone elastomer having hook ends that engage the loop top of the engineered fabric. Alternatively, a silicone elastomer may be attached to an anchor having a hooked base, which is attached to the loop top fabric.

D. Deep Fascia Repair Systems

Figure 20:
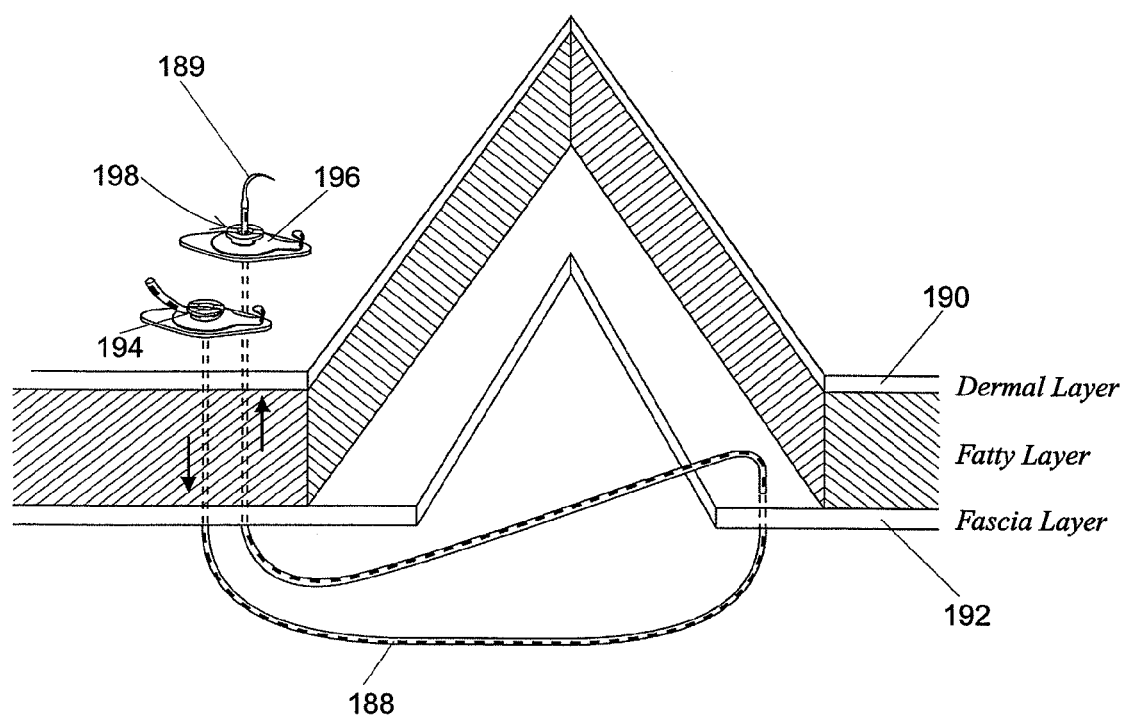
FIG. 20 is a schematicized perspective view of a system according to another embodiment of this invention illustrating use of the invention to move fascia.

The system of this invention may be used to provide deep fascia repair and deep fascia dynamic wound reduction. In one embodiment, illustrated in FIG. 20, a tubular silicone elastomer 188 is coupled to a trocar, passed through the dermis 190, looped through the fascia 192, and presented through the center opening 194 of an anchor 196 on the edge of the wound, where it is then secured to a locking rivet 198. Alternatively, the efac may be secured using an anchor having a locking wire or other suitable structure. The efac may be used to apply tension to sub-dermal structures (deep fascia) but the efac tension may be adjusted from above the skin by increasing or de-creasing the tension at the locking rivet.

Use of a hollow or tubular efac 188 to pass through the tissue allows the tube to flatten as it enters and exits tissue, so that the load is better distributed. In addition, the anchor acts as a grommet, removing the point load from the exit hole to reduce the occurrence of localized failures, and also allows adjustment of the tension across the wound. Reducing localized failures also reduces scarring.

The combination of an efac and an anchor creates a linear plane of pull, so that the skin is moved and stretched and the wound is reduced across the shortest possible distance, and it is unnecessary to follow the contour of a body cavity. This is important in situations such as in the case of severely emaciated patients with a retracted abdominal wound and in cases where a large cavity exists after removal of a tumor. In such situations, a locking rivet and hydrocolloid adhesive anchor can be used to terminate and tension the efac at the point where it passes through the skin.

E. Fasciotomy Systems

Embodiments of this invention may be used to provide wound stabilization to prevent severe retraction from occurring after a fasciotomy which provides release of intercompartmental pressure, but provides such release in an irreversible procedure. Complications arise under current fasciotomy methods from the loss of tension to the skin at the wound site. Applied pre-operatively, embodiments of this invention provide a controlled release of skin tension to levels that restore vascular function without un-tensioning the skin system to the point that severe retraction occurs. As compartment pressures are reduced, systems of this invention provide tension to restructure original configuration of the skin.

In an embodiment used in the closure of a fasciotomy, the method of gradual wound closure eliminates the need for later suturing because the system approximates the edges of the wound, allowing the wound to heal as if sutures were in place. Elimination of delayed closure provides treatment in a single surgical intervention. Controlled radial pressure promotes migration of the edema fluid across the cell wall, enabling faster absorption by the lymphatic system. Thus, when applied to a fasciotomy, devices according to this invention accelerate the reduction in swelling. Retraction of the skin is controlled, which reduces the amount of reapproximation required to close the wound after swelling is reduced and compartment pressures are normalized.

F. Other Systems and Applications

A system according to this invention may provide stabilization of abdominal procedures. For example, a system may be used to restore radial abdominal integrity during prolonged interventions for complications such as abdominal infections management or which require large abdominal access. This system increases patent comfort and mobility by providing abdominal containment and support, and maintains normal skin tensions during intervention to minimize retraction.

Another system may provide stability to sternum non unions. In addition, systems of this invention may be used with conventional primary wound closure methods to distribute skin system tensions to healthy skin beyond the wound, thereby minimizing stress at the wound site and reducing dehiscence. A system of this invention may be applied preoperatively to tension skin and create surplus tissue, allowing excisions to be covered and closed in a conventional manner. Embodiments of this invention may also be used as a dressing retention system by providing efac lacing across the wound site, which passes over the wound dressing and secures it in position.

In another embodiment, an elastic tensor bandage is bonded to a hydrocolloid membrane and stretched across dressing placed on the open portion of a wound, providing dynamic wound closure.

In yet another embodiment, a tensioned silicone membrane including either a hook and loop interface or a post and hole interface to a wound edge tape is stretched across a wound and joined to the tape, providing dynamic wound closure. This embodiment may be used for treating and controlling hypertrophic and keloid scars. In this embodiment the membrane is a silicone gel membrane.

The systems and methods of moving and stretching plastic tissue according to this invention are not confined to the embodiments described herein but include variations and modifications within the scope and spirit of the foregoing description and the accompanying drawings. For instance, the scale of the components of the invention can vary quite substantially depending on the nature and location of the tissue with which the invention is used. The configuration of the tissue attachment structures can also be varied for the same reasons and for aesthetic reasons. While most of the elements of the illustrative embodiments of the anchors of this invention depicted in the drawings are functional, aspects of the shape and appearance of the illustrative embodiments are nonfunctional and ornamental.

The materials from which the components used in practicing this invention are made can be those described above as well as others, including materials not yet developed that have appropriate properties of strength, elasticity and the like that will be apparent to those skilled in the art in light of the foregoing. For instance, useful materials generally must be sterile or sterilizable and non-reactive. The illustrated components are typically intended to be reusable, but the invention can also be practiced using disposable components, such as, for instance, metal or plastic anchors supplied in a sterile package and optionally having pressure sensitive adhesive covered by a peel-off film on one surface of the anchor to protect the adhesive until the anchor is to be used.

The invention claimed is:

1. A method for stretching plastic tissue comprising:
   (a) evaluating a needed direction of stretching of the tissue;
   (b) determining a number of anchors to employ;
   (c) installing at least one anchor to the tissue with surgical adhesive;
   (d) securing at least one elastomeric force applying component to the at least one anchor without knotting the force applying component;
   (e) adjusting tension by removing and re-securing the same at least one elastomeric force applying component to the at least one anchor.

2. The method of claim 1 further comprising dressing the area of application prior to securing the elastomeric force applying component.

3. The method of claim 1 wherein the elastomeric force applying component is at least one monostrand elastomer having two ends.

4. The method of claim 3 wherein the securing the elastomeric force applying component further comprises securing one end of the elastomer to a cleat in a first anchor, lacing the elastomer around a hook of a second anchor, and securing the other end of the elastomer to a cleat in a third anchor.

5. The method of claim 1 wherein the elastomeric force applying component further comprises a tension indication feature.

6. The method of claim 5 wherein the adjusting tension further comprises referring to a tension application table to determine extension needed to apply a desired force.

7. The method of claim 1 wherein the adjusting tension further comprises referring to a tension indication feature of the elastomeric force applying component.

8. The method of claim 1 wherein the tension is infinitely adjustable within an elastic limit of the elastomeric force applying component.

9. The method of claim 1 wherein the elastomeric force applying component comprises at least two elastomers each having two ends.

10. The method of claim 9 wherein securing the elastomeric force applying component further comprises: securing one end of a first elastomer to a first anchor and securing the other end of the first elastomer to a second anchor; and securing one end of a second elastomer to a third anchor and securing the other end of the second elastomer to a fourth anchor.

11. The method of claim 9 wherein securing the elastomeric force applying component further comprises securing one end of each elastomer to a first anchor and securing the other end of each elastomer to a second anchor.

12. The method of claim 1 wherein the elastomeric force applying component is an elastic suture.

13. The method of claim 1 wherein said securing the elastomeric force applying component further comprises securing a first end of the elastomeric force applying component to a first anchor and securing a second end of the elastomeric force applying component to a second anchor.

14. The method of claim 1 further comprising a plurality of anchors attached to a strip of surgical adhesive.

15. The method of claim 1 wherein the at least one anchor further comprises a cleat for securing the elastomeric force applying component.

16. The method of claim 1 wherein the at least one anchor further comprises a hook for engaging the elastomeric force applying component.

17. The method of claim 1 wherein the at least one anchor further comprises an eye.

18. The method of claim 1, wherein evaluating the needed stretching of the tissue comprises evaluating the needed stretching of healthy tissue.

* * * * *